US012658281B2

(12) United States Patent
Amimeur et al.

(10) Patent No.: US 12,658,281 B2
(45) Date of Patent: Jun. 16, 2026

(54) DETERMINING PROTEIN STRUCTURE AND PROPERTIES BASED ON SEQUENCE

(71) Applicant: Just-Evotec Biologics, Inc., Seattle, WA (US)

(72) Inventors: Tileli Amimeur, Seattle, WA (US); Jeremy Martin Shaver, Lake Forest Park, WA (US); Randal Robert Ketchem, Snohomish, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 1136 days.

(21) Appl. No.: 16/975,989

(22) PCT Filed: Feb. 26, 2019

(86) PCT No.: PCT/US2019/019688
§ 371 (c)(1),
(2) Date: Aug. 26, 2020

(87) PCT Pub. No.: WO2019/165476
PCT Pub. Date: Aug. 29, 2019

(65) Prior Publication Data
US 2021/0043272 A1      Feb. 11, 2021

Related U.S. Application Data

(60) Provisional application No. 62/635,529, filed on Feb. 26, 2018.

(51) Int. Cl.
*G16B 15/20*          (2019.01)
*G16B 5/00*          (2019.01)

(52) U.S. Cl.
CPC .............. *G16B 15/20* (2019.02); *G16B 5/00* (2019.02)

(58) Field of Classification Search
None
See application file for complete search history.

(56) References Cited

U.S. PATENT DOCUMENTS

2003/0036093 A1      2/2003 Floudas et al.

FOREIGN PATENT DOCUMENTS

CA          3092098  C      7/2023
JP      2002034876  A      2/2002
(Continued)

OTHER PUBLICATIONS

Kumar Mishra, Sushil. "In Silico Engineering of Proteins That Recognize Small Molecules." InTech EBooks. IntechOpen, 2012. Web. (Year: 2012).*

(Continued)

*Primary Examiner* — Anna Skibinsky
*Assistant Examiner* — Joseph Pulliam
(74) *Attorney, Agent, or Firm* — Schwegman Lundberg & Woessner, P.A.

(57)          ABSTRACT

Technologies are described related to determining protein structure and properties based on sequences of proteins. In various implementations, a first model can be generated to determine structural features of proteins based on amino acid sequences of the proteins. Additionally, a second model can be generated to determine biophysical properties of proteins based on structural features of the proteins. In particular implementations, an amino acid sequence of a particular protein can be utilized by the first model to determine one or more structural features of the protein. The one or more structural features of the protein generated by the first model can be utilized by the second model to determine at least one biophysical property of the protein.

18 Claims, 8 Drawing Sheets

(56) References Cited

FOREIGN PATENT DOCUMENTS

| JP | 2002523057 A | 7/2002 |
| JP | 2011133962 A | 7/2011 |
| KR | 20160131837 A | 11/2016 |
| WO | WO-0234876 A2 | 5/2002 |
| WO | 02034876 A3 | 11/2003 |
| WO | WO-2019165476 A1 | 8/2019 |

OTHER PUBLICATIONS

Eswar N, Webb B, Marti-Renom MA, Madhusudhan MS, Eramian D, Shen MY, Pieper U, Sali A. Comparative protein structure modeling using Modeller. Curr Protoc Bioinformatics. Oct. 2006;Chapter 5:Unit-5.6 (Year: 2006).*

Khor BY, Tye GJ, Lim TS, Choong YS. General overview on structure prediction of twilight-zone proteins. Theor Biol Med Model. Sep. 4, 2015;12:15 (Year: 2015).*

Capriotti E, Altman RB. Improving the prediction of disease-related variants using protein three-dimensional structure. BMC Bioinformatics. 2011;12 Suppl 4(Suppl 4):S3. (Year: 2011).*

Abriata LA, Bovigny C, Dal Peraro M. Detection and sequence/structure mapping of biophysical constraints to protein variation in saturated mutational libraries and protein sequence alignments with a dedicated server. BMC Bioinformatics. Jun. 17, 2016;17(1):242 (Year: 2016).*

Le SQ, Dang CC, Gascuel O. Modeling protein evolution with several amino acid replacement matrices depending on site rates. Mol Biol Evol. Oct. 2012;29(10):2921-36. (Year: 2012).*

He B, Mortuza SM, Wang Y, Shen HB, Zhang Y. NeBcon: protein contact map prediction using neural network training coupled with naïve Bayes classifiers. Bioinformatics. Aug. 1, 2017;33(15):2296-2306. (Year: 2017).*

Eramian D, Shen MY, Devos D, Melo F, Sali A, Marti-Renom MA. A composite score for predicting errors in protein structure models. Protein Sci. Jul. 2006; 15(7):1653-66. (Year: 2006).*

Jurtz, Vanessa Isabell et al. "An Introduction to Deep Learning on Biological Sequence Data: Examples and Solutions." Bioinformatics (Oxford, England) 33.22 (2017): 3685-3690. Web. (Year: 2017).*

Du, Xiuquan et al. "DeepPPI: Boosting Prediction of Protein-Protein Interactions with Deep Neural Networks." Journal of chemical information and modeling 57.6 (2017): 1499-1510. Web. (Year: 2017).*

Cang, Zixuan, and Guo-Wei Wei. "TopologyNet: Topology Based Deep Convolutional and Multi-Task Neural Networks for Biomolecular Property Predictions." PLoS computational biology 13.7 (2017): e1005690-e1005690. Web. (Year: 2017).*

Torng, Wen, and Russ B Altman. "3D Deep Convolutional Neural Networks for Amino Acid Environment Similarity Analysis." BMC bioinformatics 18.1 (2017): 302-302. Web. (Year: 2017).*

"International Application Serial No. PCT/US2019/019688, International Search Report mailed Jul. 26, 2019", 5 pgs.

"International Application Serial No. PCT/US2019/019688, Written Opinion mailed Jul. 26, 2019", 7 pgs.

Dill, K A, et al., "The Protein-Folding Problem, 50 Years On", Science, vol. 338, No. 6110, (Nov. 23, 2012), 1042-1046.

Yang, Yang, et al., "PON-Sol: prediction of effects of amino acid substitutions on protein solubility", Bioinformatics, vol. 32. No. 13., (Feb. 19, 2016), 2032-2034.

"European Application Serial No. 19714891.9, Response filed Apr. 12, 2021 to Communication pursuant to Rules 161(1) and 162 EPC mailed Apr. 7, 2021", 33 pgs.

"Canadian Application Serial No. 3,092,098, Office Action mailed Sep. 22, 2021", 6 pgs.

"Canadian Application Serial No. 3,092,098, Response filed Jan. 17, 2022 to Office Action Mailed Sep. 22, 2021", 33 pgs.

"European Application Serial No. 19714891.9, Response filed May 10, 2024 to Communication Pursuant to Article 94(3) EPC mailed Nov. 13, 2023", 10 pages.

"European Application Serial No. 19714891.9, Communication Pursuant to Article 94(3) EPC mailed Nov. 13, 2023", 8 pgs.

"Japanese Application Serial No. 2020-544750, Notification of Reasons for Refusal mailed Apr. 11, 2023", with English translation, 12 pages.

"Japanese Application Serial No. 2020-544750, Response filed Jul. 7, 2023 to Notification of Reasons for Refusal mailed Apr. 11, 2023", with machine English translation, 22 pages.

* cited by examiner

400

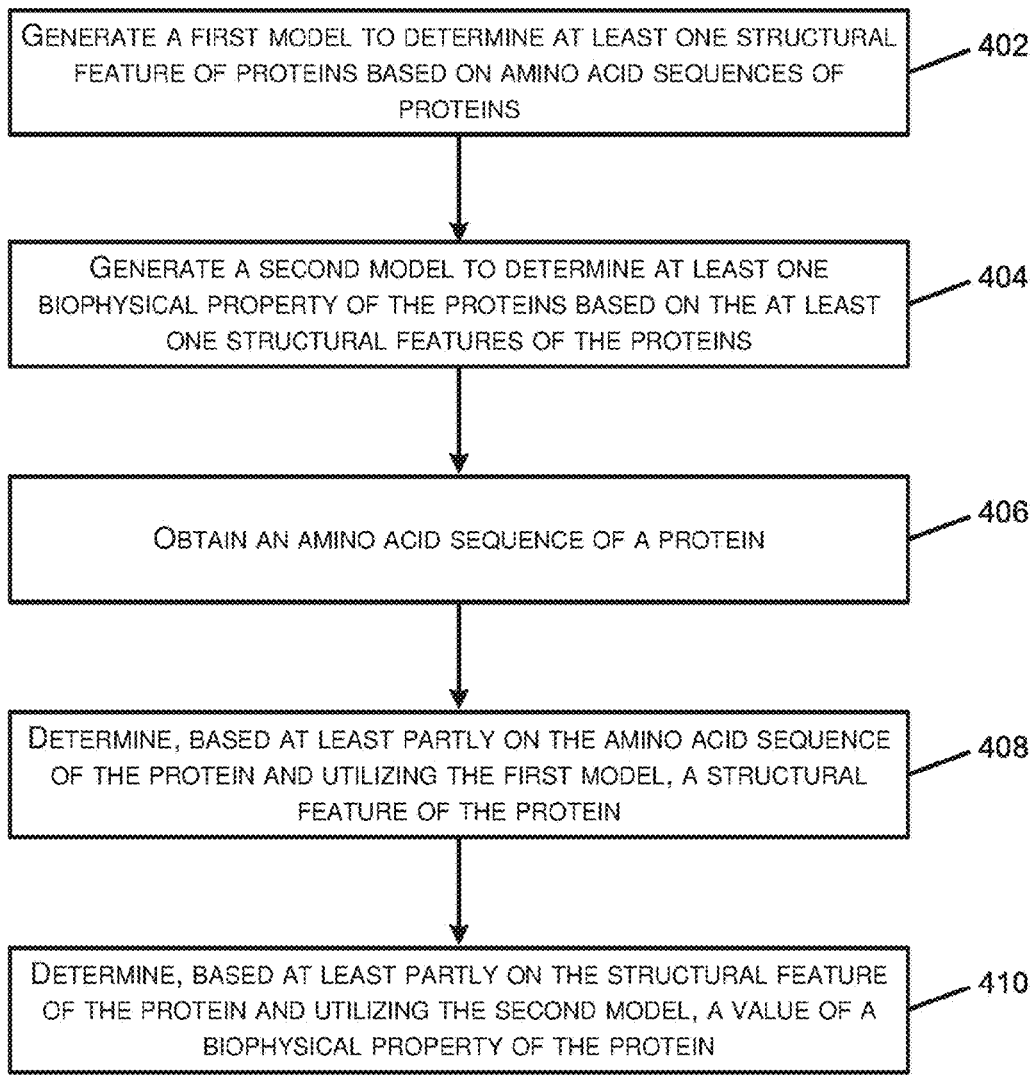

GENERATE A FIRST MODEL TO DETERMINE AT LEAST ONE STRUCTURAL FEATURE OF PROTEINS BASED ON AMINO ACID SEQUENCES OF PROTEINS — 402

GENERATE A SECOND MODEL TO DETERMINE AT LEAST ONE BIOPHYSICAL PROPERTY OF THE PROTEINS BASED ON THE AT LEAST ONE STRUCTURAL FEATURES OF THE PROTEINS — 404

OBTAIN AN AMINO ACID SEQUENCE OF A PROTEIN — 406

DETERMINE, BASED AT LEAST PARTLY ON THE AMINO ACID SEQUENCE OF THE PROTEIN AND UTILIZING THE FIRST MODEL, A STRUCTURAL FEATURE OF THE PROTEIN — 408

DETERMINE, BASED AT LEAST PARTLY ON THE STRUCTURAL FEATURE OF THE PROTEIN AND UTILIZING THE SECOND MODEL, A VALUE OF A BIOPHYSICAL PROPERTY OF THE PROTEIN — 410

COMPUTING DEVICE(S) 602

PROCESSING
UNIT(S)
604

PROTEIN PROPERTIES
MODEL GENERATING
SYSTEM 130

STRUCTURAL FEATURES
MODEL GENERATING
SYSTEM 136

PROTEIN ANALYSIS
SYSTEM 142

MEMORY 606

INPUT / OUTPUT
DEVICES
608

NETWORK INTERFACE
610

DEVICE INTERFACE
614

NETWORK 612

DETERMINING PROTEIN STRUCTURE AND PROPERTIES BASED ON SEQUENCE

CROSS-REFERENCE TO RELATED APPLICATION(S) AND PRIORITY CLAIM

This application is a U.S. national stage filing under 35 U.S.C. 371 from International Application No. PCT/US2019/019688, filed on 26 Feb. 2019, and published as WO 2019/165476 A1 on 29 Aug. 2019, which claims priority to U.S. Provisional Application No. 62/635,529 filed on Feb. 26, 2018 and entitled "Determining Protein Structure and Properties Based on Sequence," the entirety of which are incorporated herein by reference.

BACKGROUND

Proteins are comprised of a sequence of amino acids that are linked via chemical bonds. The amino acid sequence of a particular protein is based on a sequence of nucleotides in the deoxyribonucleic acid (DNA) from which the protein is expressed. The functionality and structure of a protein can be based on the amino acid sequence of the protein. Proteins can have a variety of functions within an organism, such as regulation of enzymatic activity or cellular signaling. Some proteins can also be used therapeutically to treat a biological condition. For example, proteins, such as an antibody, can, in some cases, bind to a pathogen to target the pathogen for destruction by other agents in the organism, such as T cells or macrophages. In another example, proteins can bind to a molecule to transport the molecule to a targeted location in an organism to alleviate phenotypes of a biological condition.

Atomic structures of proteins are often determined using complex calculations on data derived from X-ray crystallography, nuclear magnetic resonance (NMR) spectroscopy, or cryo-electron microscopy. The atomic structures of many proteins are stored in a publicly available database called the Protein Data Bank. The determination of atomic structures of proteins can be a time-consuming, difficult, and costly process, often taking months up to years to determine the structural features of a single protein. Properties of proteins can be determined using specific analytical tests for each property being determined. For example, stability of a protein can be determined through differential scanning fluorimetry and molecular weight of a protein can be determined using size exclusion chromatography. The characterization of proteins can also be time-consuming, difficult, and costly because for each protein being characterized, multiple tests are performed to determine the properties of a particular protein. The characterization of a single protein can take weeks up to months in order to determine the properties of the protein.

BRIEF DESCRIPTION OF THE DRAWINGS

FIG. 4 is a flow diagram of a first example process to generate a first model to predict structural features of a protein based on amino acid sequence and to generate a second model to predict values of biophysical properties of the protein based on the structural features of the protein.

DETAILED DESCRIPTION

Figure 1:
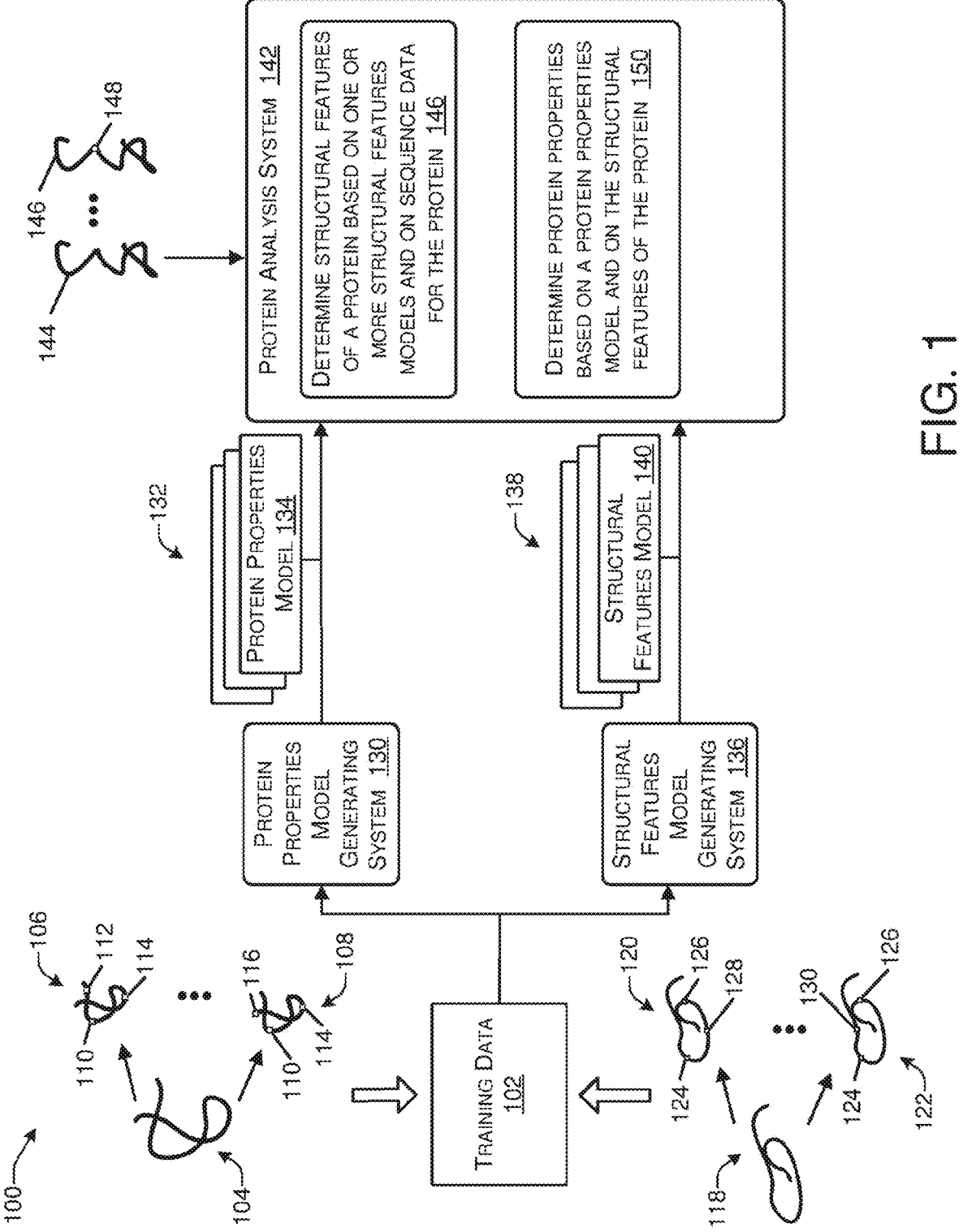
FIG. 1 is a diagram of implementations of an architecture to determine protein structure and properties based on protein sequence.

The concepts described herein are directed to determining protein structure and properties based on protein sequence. In implementations, systems and techniques described herein utilize differences between sequences of proteins and variants of the proteins to determine structural features of proteins. Additionally, systems and techniques described herein utilize differences between structural features of proteins and variants of the proteins to determine biophysical properties of proteins. In particular implementations, machine learning can be utilized to generate models for determining structural features of proteins from changes in protein sequence and for determining biophysical properties of proteins from changes in structural features of the proteins.

Particular structural features of proteins are typically determined from the atomic structure of the proteins. For example, an atomic structure of a protein can serve as a template and the structural features of the protein can be determined by utilizing intensive computational processes that minimize the energy related to the folding of the template. Since determining the atomic structures of proteins can be a lengthy and complex process, utilizing these atomic structures to determine structural features of the proteins can be limiting. That is, the number of proteins for which structural features can be determined is a very limited subset of the total number of possible proteins that can be analyzed. Additionally, since characterizing proteins can also be a lengthy and complex process, utilizing conventional analytical techniques to determine biophysical properties of larger numbers of proteins can also be prohibitive. Accordingly, utilizing machine learning techniques that implement predictive models to determine structural features of proteins and biophysical properties of proteins can minimize the number of physical resources utilized and the amount of time needed to determine the structure of proteins and to characterize the proteins.

However, the amount of data utilized to train machine learning models is limited. In particular, the challenges in determining structural features of proteins and in determining biophysical properties of proteins results in a sparse amount of data that can be utilized to train machine learning models to determine structural features of proteins and biophysical properties of proteins. Sequence data for proteins is more readily available and the techniques utilized to determine sequences of proteins are less costly and time consuming than the techniques utilized to determine structural features and biophysical properties of proteins. Thus, it can be possible to utilize relationships between protein sequences and structural features of proteins to train machine learning models that can determine structural features of proteins and biophysical properties of proteins based on protein sequences. In various implementations described herein, techniques and systems are described that generate models for determining structural features and biophysical properties of proteins based on the sequence of the proteins.

In some situations, though, the structural features of proteins do not correspond directly to the sequences of the proteins. For example, a single protein can have different structural features at the same positions in the sequence of the protein due to crystal packing effects. That is, a protein having a single sequence can have varying structural features. In these scenarios, machine learning models can provide inaccurate results for structural features and biophysical properties that are determined based on protein sequence. Thus, additional systems and techniques are described herein that correct for the inaccuracies that can occur with respect to machine learning models used to determine structural features and biophysical properties of proteins based on protein sequences in situations where a single protein can have different structural features due to crystal packing effects.

In various implementations, techniques and systems are described herein that implement relative models to determine structural features and biophysical properties of proteins based on sequences of proteins. To illustrate, a number of proteins can be expressed in addition to many variants of each of the proteins. Additionally, structural features of the proteins and the variants of the proteins along with biophysical properties of the proteins and the variants of the proteins can be determined. Differences between the sequences of a protein and its variants can be correlated with changes to structural features and changes to biophysical properties between the protein and its variants. The correlations between sequence differences and changes to structural features of proteins and biophysical properties of the proteins for multiple proteins and their variants can be utilized to train models that determine structural features and biophysical properties of additional proteins based on the sequences of the additional proteins.

By determining correlations between differences of protein sequences and changes to structural features and biophysical properties of variants of the proteins, relative data can be used to generate models that can utilize protein sequences to determine structural features and biophysical properties of proteins. The use of relative data to generate the models to determine structural features and biophysical properties of proteins from protein sequences removes the inaccuracies that can result from simply using raw structural features data and biophysical properties data that has been correlated to sequence data to generate models for determining the structure features and biophysical properties of proteins from the sequences of the proteins.

FIG. 1 is a diagram of implementations of an architecture 100 to determine protein structure and properties based on protein sequence. In the architecture 100, training data 102 can be utilized to generate models that can determine structural features of proteins and models that can determine properties of proteins. The training data 102 can be derived from a first protein 104 and variants of the first protein 104. The first protein 104 can have a number of variants from a first variant 106 to an $N^{th}$ variant 108. The first variant 106 can differ from the first protein 104 at least at positions 110, 112, 114 and the $N^{th}$ variant 108 can differ from the first protein 104 at least at positions 110, 114, 116. The training data 102 can also be derived from a second protein 118 and variants of the second protein 118. The second protein 118 can have a number of variants from a first variant 120 up to an $N^{th}$ variant 122. The first variant 120 can differ from the second protein 118 at least at positions 124, 126, 128 and the $N^{th}$ variant 122 can differ from the second protein 118 at least at positions 124, 126, 128. In illustrative examples, the first protein 104 and its variants 106 to 108 along with the biophysical properties of the second protein 118 and its variant 120 to 122 can include antibodies. In particular illustrative examples, the first protein 104 and its variants 106 to 108 along with the biophysical properties of the second protein 118 and its variant 120 to 122 can include immunoglobin type antibodies (Ig). In certain implementations, the light chains can be classified as λ or κ.

In particular implementations, the training data 102 can include amino acid sequences of the first protein 104 and the second protein 118. The amino acid sequences of the first protein 104 and the second protein 118 can indicate the particular amino acids located at individual positions of the first protein 104 and the second protein 118. Particular techniques for determining a protein sequence using mass spectrometry can be found in Hunt, D F et al. "Protein Sequencing by Tandem Mass Spectrometry." *Proceedings of the National Academy of Sciences of the United States of America* 83.17 (1986): 6233-6237. Print. Additionally, the sequences of the first protein 104, the second protein 118, and their variants can be determined using Edman degradation as described in Berg J M, Tymoczko J L, Stryer L. Biochemistry. 5th edition. New York: W H Freeman; 2002. Section 4.2, Amino Acid Sequences Can Be Determined by Automated Edman Degradation. Available from: www.ncbi.nlm.nih.gov/books/NBK22571/. Further, the sequences of the first protein 104, the second protein 118, and their variants can be determined from a sequence of nucleotides, such as a deoxyribonucleic acid (DNA) sequence or a ribonucleic acid (RNA) sequence associated with the first protein 104, the second protein 118, and their variants, as described in Smith, A. (2008) Nucleic acids to amino acids: DNA specifies protein. Nature Education 1(1): 126.

Figure 2:
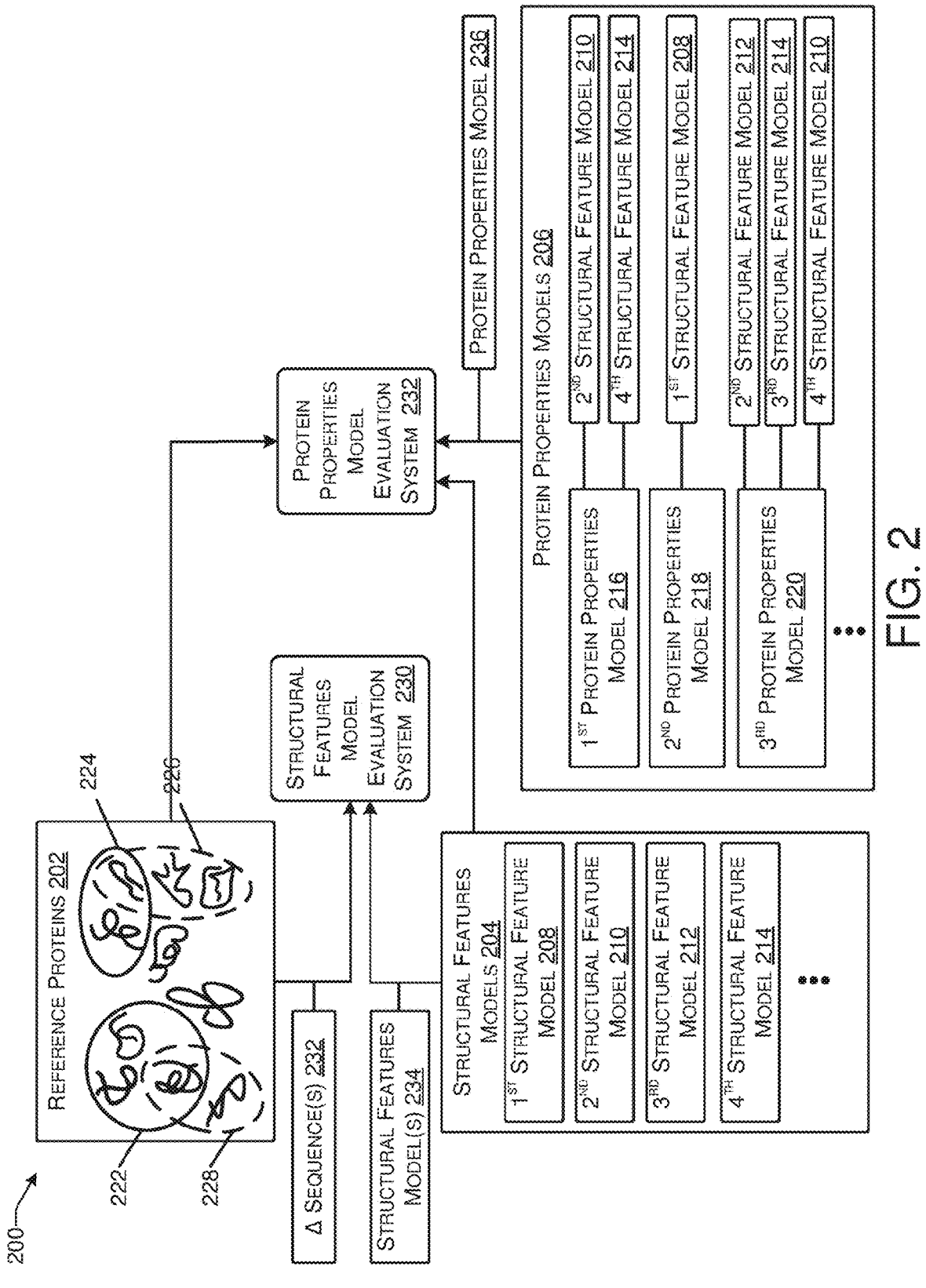
FIG. 2 is a diagram of implementations of an architecture to determine models to determine protein structure and properties based on changes to protein sequences.

The training data 102 can also include structural features of the first protein 104 and its variants 106 to 108 in addition to the structural features of the second protein 118 and its variants 120 to 122. Although the illustrative example of FIG. 2 shows that the first protein 104 and the second protein 118 have two variants, in other examples, the first protein 104 and the second protein 118 can have different numbers of variants, such as tens of variants, hundreds of variants, or more. The structural features of the first protein 104, variants 106 to 108, the second protein 118, and variants 120 to 122 can include α-helixes, β-turns, β-sheets, Ω-loops, additional structural features, or combinations thereof. The structural features of the first protein 104, variants 106 to 108, the second protein 118, and variants 120 to 122 can also indicate hydrophobic regions, polar regions, charged regions, additional structural features, or combinations thereof of the first protein 104, variants 106 to 108, the second protein 118, and variants 120 to 122. The structural features can indicate a number of positions or one or more regions of a protein associated with a type of secondary structure or a type of tertiary structure of the first protein 104, variants 106 to 108, the second protein 118, and variants 120 to 122. Secondary structure of the first protein 104, variants 106 to 108, the second protein 118, and variants 120 to 122 can be determined by a number of methods including those described in Determination of the secondary structure of proteins by laser Raman spectroscopy; J. L. Lippert, D. Tyminski, and P. J. Desmeules; *Journal of the American Chemical Society* 1976 98 (22), 7075-7080 DOI: 20 10.1021/ja00438a057 and described in Alberts B, Johnson A, Lewis J, et al. Molecular Biology of the Cell. 4th edition. New York: Garland Science; 2002. Analyzing Protein Structure and Function. Available from: www.ncbi.nlm.nih.gov/books/NBK26820/. In situations where an atomic structure of a protein has been determined, structural features of the protein based on the atomic structure can also be determined according to computational techniques that minimize the energy related to the folding of the protein.

Further, the training data 102 can include biophysical properties of the first protein 104 and its variants 106 to 108 along with the biophysical properties of the second protein 118 and its variant 120 to 122. The biophysical properties of the first protein 104 and its variants 106 to 108 along with the biophysical properties of the second protein 118 and its variant 120 to 122 can be obtained from analytical tests that can include a number of assays that produce data about the first protein 104 and its variants 106 to 108 along with the biophysical properties of the second protein 118 and its variant 120 to 122. In various implementations, the biophysical properties of the first protein 104 and its variants 106 to 108 along with the biophysical properties of the second protein 118 and its variant 120 to 122 can include molecular weight that can be determined using size exclusion chromatography and/or turbidity that can be measured using a UV-Vis spectrophotometer. In additional implementations, the biophysical properties of the first protein 104 and its variants 106 to 108 along with the biophysical properties of the second protein 118 and its variant 120 to 122 can include measures of stability that can be determined by differential scanning fluorimetry (DSF) or a Chemical Unfolding assay. Further, the biophysical properties of the first protein 104 and its variants 106 to 108 along with the biophysical properties of the second protein 118 and its variant 120 to 122 can include measures of interactions between regions of these individual proteins as determined by self-interaction nanoparticle spectroscopy (SINS).

The architecture 100 can include a protein properties model generating system 130 that can obtain the training data 102. The protein properties model generating system 130 can utilize the training data 102 to produce a group of protein properties models 132 that can include the protein properties model 134. The group of protein properties models 132 can determine biophysical properties of proteins based at least partly on structural features of the proteins. In particular implementations, the protein properties model generating system 130 can analyze the training data 102 to determine relationships between structural features of the proteins associated with the training data 102 and the biophysical properties of the proteins associated with the training data 102. The relationships between the structural features of the proteins associated with the training data 102 and the biophysical properties of the proteins associated with the training data 102 can be represented by one or more equations that include one or more variables and one or more weights corresponding to the one or more variables. The one or more weights can indicate an amount of influence on determining a biophysical property by a particular structural feature for linear models or by some combination of linear and nonlinear structural features for nonlinear models that is represented by a respective variable in the group of protein properties models. 132.

The architecture 100 can also include a structural features model generating system 136 that can obtain the training data 102 and utilize the training data 102 to generate a group of structural features models 138 that can include the structural features model 140. The group of structural features models 138 can determine structural features of proteins based at least partly on sequences of the proteins. In particular implementations, the protein properties model generating system 136 can analyze the training data 102 to determine relationships between sequences of the proteins associated with the training data 102 and the structural features of the proteins associated with the training data 102. The relationships between the sequences of the proteins associated with the training data 102 and the structural features of the proteins associated with the training data 102 can be represented by one or more equations that include one or more variables and one or more weights corresponding to the one or more variables. The one or more weights can indicate an amount of influence on structural features by a sequence or a particular portion of a sequence for linear models or by some combination of linear and/or nonlinear structural features for nonlinear models that is represented by a respective variable in the group of structural features models 138.

In various implementations, the group of structural features models 138 can include a single model for each structural feature being determined. To illustrate, the group of structural features models 138 can include a structural features model to determine hydrophobicity of regions of a protein. In another illustrative example, the group of structural features models 138 can include a structural features model to determine polar regions of a protein. In additional situations, the group of structural features models 138 can include a structural features model to determine charged regions of a protein. Further, the group of structural features models 138 can include one or more first models to determine structural features of heavy chains of antibodies and one or more second models to determine structural features of light chains of antibodies. In certain implementations, individual models of the group of structural features models 138 can include a random forests model. In additional implementations, individual models of the group of structural features models 138 can include a neural network or a convolution neural network. In illustrative implementations, individual models of the group of structural features models 138 can include a combination of models. For example, an individual model of the group of structural features models 138 can include a combination of a k-Nearest Neighbors model coupled with a neural network.

In various implementations, individual models of the group of protein properties models 132 can obtain input from one or more of the group of structural features models 138. In particular implementations, individual biophysical properties being determined utilizing particular protein properties models 132 can each be associated with a respective number of one or more structural features models 138. For example, a protein properties model 132 related to determining a temperature at which a protein begins to unfold can utilize input from a first structural features model 138 related to determining hydrophobicity of proteins, a second structural features model 138 related to determining polar regions of proteins, and a third structural features model 138 related to determining charged regions of proteins. In various implementations, the group of protein properties models 132 can include a random forests model. In additional implementations, the group of protein properties models 132 can include a factor-based model, such as a Parafac model, a partial least squares (PLS) model, or a non-parametric linkage scores (NPLS) model.

The group of protein properties models 132 can be determined, in implementations, based at least partly on analyzing differences between structural features of the first protein 104 and its variants 106 to 108 with respect to individual biophysical properties and analyzing differences between structural features of the second protein 118 and its variants 120 to 122 with respect to individual biophysical properties. In particular examples, the protein properties model generating system 130 can analyze differences between hydrophobicity between the first protein 104 and its variants 106 to 108 and differences between hydrophobicity of the second protein 118 and its variants 120 to 122 to generate a model that determines a temperature at which a protein unfolds. In additional implementations, the group of structural features models 138 can be determined, by analyzing differences in sequences of the first protein 104 and its variants 106 to 108 in relation to a structural feature and differences in sequences of the second protein 118 and its variants 120 to 122 in relation to the structural feature. In an illustrative example, the structural features model generating system 136 can analyze differences between sequences of the first protein 104 and its variants 106 to 108 and differences between sequences of the second protein 118 and its variants 120 to 122 to determine changes in polar regions of proteins.

The architecture 100 can also include a protein analysis system 142 that can utilize the group of protein properties models 132 and the group of structural features models 138 to determine biophysical properties of proteins based on sequences of the proteins, such as an additional protein 144. In particular, at 146, the protein analysis system 142 can determine structural features of the additional protein 144 based on one or more structural features models and on sequence data for the additional protein 144. The protein analysis system 142 can also utilize as input differences between the sequence of the additional protein 144 and the sequence of at least one variant of the additional protein, such as the variant protein 146 having an amino acid sequence that varies from the amino acid sequence of the additional protein 144 at least at position 148. Additionally, at 150, the protein analysis system 142 can determine biophysical properties of the additional protein 144 based at least partly on structural features of the additional protein 144 that are determined at operation 146. The protein analysis system 142 can also determine biophysical properties of the additional protein 144 based at least partly on differences between structural features of the additional protein 144 and at least one variant of the additional protein 144, such as the variant 146.

In an illustrative example, a sequence of the additional protein 144 and a sequence of the variant 146 can be obtained by the protein analysis system 142. Further, a request to determine one or more biophysical properties of the additional protein 144 can also be obtained by the protein analysis system 142. Based at least partly on the one or more biophysical properties associated with the input, the protein analysis system 142 can identify structural features that can be utilized to determine the one or more biophysical properties. The protein analysis system 142 can then utilize the structural features models selected from the group of structural features models 138 that correspond to the one or more biophysical properties. The protein analysis system 142 can proceed to determine the structural features from the structural features models selected from the group of structural features models 138 based at least partly on differences between the sequence of the additional protein 144 and the sequence of the variant 146. Subsequently, the protein analysis system 142 can utilize the structural features obtained using the group of structural features models as input to a protein properties model 132 that corresponds to the biophysical property being determined. In particular implementations, the protein analysis system 142 can determine differences between structural features of the additional protein 144 and its variant 146 as input to the protein properties model 132 that corresponds to the biophysical property being determined. The protein analysis system 142 can then determine a value or a change in the value of the biophysical property for the additional protein 144 based at least partly on the protein properties model 132 that corresponds to the biophysical property being determined and the structural features or differences in structural features determined at operation 146.

FIG. 2 is a diagram of implementations of an architecture 200 to determine models to determine protein structure and properties based on changes to protein sequences. The architecture 200 can include reference proteins 202 that can be used to train and test models for determining structural features of proteins based on sequences of the proteins, such as the structural features models 204. The reference proteins 202 can also be used to train and test models for determining biophysical properties of proteins based on models of the structural features determined from the reference proteins 202, such as the protein properties models 206. The structural features models 204 can include at least a first structural feature model 208, a second structural feature model 210, a third structural feature model 212, and a fourth structural feature model 214. Additionally, the protein properties models 206 can include at least a first protein properties model 216, a second protein properties model 218, and a third protein properties model 220.

Individual protein properties models 206 can be associated with certain structural features models 204, in various implementations. That is, particular structural features can be indicative of particular biophysical properties of proteins. Thus, the structural features models 204 that correspond to the structural features indicative of a particular biophysical property are associated with the protein properties model 206 related to that particular biophysical property. In an example, a number of polar regions of a protein can correspond to a temperature at which the protein unfolds. Continuing with this example, a structural feature model 204 that determines the number of polar regions of a protein can then be associated with a protein properties model 206 that is related to determining the temperature at which the protein unfolds. In the illustrative example of FIG. 2, the first protein properties model 216 is associated with the second structural feature model 210 and the fourth structural feature model 214. Additionally, the second protein properties model 218 is associated with the first structural features model 208, while the third protein properties model 220 is associated with the second structural features model 210, the third structural features model 212, and the fourth structural features model 214.

The reference proteins 202 can include a first group 222 and a second group 224. The first group 222 can include a number of proteins used to train the structural features models 204 to identify structural features of proteins and train the protein properties models 206 to determine the biophysical properties of proteins. The second group 224 can include a number of proteins used to test the structural features models 204 and the biophysical properties models 208 for accuracy.

In various implementations, different groups of the reference proteins 202 can be iteratively selected to train and test the structural features models 204 and the protein properties models 206. For example, the first group 222 can be selected to train the structural features models 204 and the protein properties models 206 and the second group 224 can be utilized to test the structural features models 204 and the protein properties models 206 for accuracy. After a first iteration using the first group 222 and the second group 224, a second iteration of training and testing can be performed using a third group 226 of the reference proteins 202 to train the structural features models 204 and the protein properties models 206 and using a fourth group 228 to test the structural features models 204 and the protein properties models 206 that were generated based on the third group 226. After performing the second iteration of training and testing, the structural features models 204 and the protein properties models 206 can be adjusted for accuracy based on differences between the results of the first iteration of training ant testing and the second iteration of training and testing. Subsequent iterations of testing and training with different combinations of the reference proteins 202 can be utilized to further refine the accuracy of the structural features models 204 and the protein properties models 206 until error of the structural features models 204 and error of the protein properties models 206 are minimized. In additional implementations, the structural features models 204 and the protein properties models 206 can be trained and tested using different groups of proteins. Thus, the structural features models 204 can be trained and tested using a first set of protein groups and the protein properties models 206 can be trained and tested using a second set of protein groups that is different from the first set of protein groups.

Although the illustrative example of FIG. 2 shows that the reference proteins 202 include ten proteins, the first group 222 and the third group 226 include three proteins, and the second group 224 and the fourth group 228 include two proteins, in other implementations, the reference proteins 202, the first group 222, the second group 224, the third group 226, and the fourth group 228 can include different numbers of proteins. In some cases, variants of the reference proteins 202 can be utilized to generate the structural features models 204 from protein sequences and to generate the protein properties models 206 to determine biophysical properties from the structural features models 204.

The architecture 200 can include a structural features model evaluation system 230 that can evaluate the structural features models 204 by training and testing the structural features models 204 using the reference proteins 202. In particular implementations, the structural features model evaluation system 230 can obtain differences between sequences of proteins and variants of the proteins to train and test one or one or more structural features models 234. For example, the structural features model evaluation system 230 can determine differences between sequences of the first group 222 of the reference proteins 202 and variants of the first group 222 and determine an accuracy of the structural features models 234 based on testing with structural features of the second group 224 of the reference proteins 202 and variants of the second group 224. After iteratively training and testing the one or more structural features models 234 using different combinations of the reference proteins 202, the structural features model evaluation system 230 can determine whether an error has been minimized for the one or more structural features models 234.

In addition, the architecture 200 can include a protein properties model evaluation system 232 that can evaluate a protein properties model 234 of the protein properties models 206 to minimize an error with respect to the protein properties model 234. For example, the protein properties model evaluation system 232 can obtain output from the structural features models 204 with respect to the reference proteins 202 and variants of the reference proteins 202 to train and test the protein properties model 234. In an illustrative implementation, the protein properties model 234 can correspond to at least the second structural feature model 210 and the protein properties model evaluation system 232 can iteratively obtain output from the second structural features model 210 for various groups of the reference proteins 202 to train and test the protein properties model 234. To illustrate, the protein properties model evaluation system 232 can obtain differences between the second structural feature for the first group 222 and variants of the first group 222 to train the protein properties model 234 and obtain differences between the second structural feature for the second group 224 and variants of the second group 224 to test the protein properties model 234. In another iteration, the protein properties model evaluation system 232 can obtain differences between the second structural feature for the third group 226 and variants of the third group 226 to train the protein properties model 234 and obtain differences between the second structural feature for the fourth group 228 and variants of the fourth group 228 to test the protein properties model 234. The protein properties model evaluation system 232 can then evaluate an amount of error between the evaluation of the protein properties model 234 with respect to the first group 222 and the second group 224 and the amount of error between the third group 226 and the fourth group 228 to minimize the error of the protein properties model 234. Additional groups can be selected from the reference proteins 202 to train and test the protein properties model 234 until an error associated with the protein properties model 234 has been minimized.

Further, the variants of the reference proteins 202 utilized to train and evaluate the structural features models 204 can be determined using various probability maps related to the structural features utilized to determine the biophysical properties associated with a particular protein properties model. For example, single variants of parent proteins can be determined at individual positions of the parent proteins for individual amino acid substitutions. That is, in particular examples, a variant can be determined for each position of the parent protein that replaces the amino acid at the respective parent protein position with different amino acids. In certain implementations, the respective parent protein positions can be replaced with every amino acid that is not included in the original position. Thus, in various implementations, a glycine at a position of the parent protein can be replaced by leucine, isoleucine, valine, aspartic acid, glutamic acid, arginine, histidine, lysine, cysteine, methionine, phenylalanine, threonine, tryptophan, tyrosine, glutamine, proline, serine, alanine, asparagine, and selenocysteine. As the amino acid at each position of the parent protein is being replaced by the different amino acids, changes in structural features can be determined. For example, a change in hydrophobicity caused by a change in an amino acid at a particular position can be determined. As different structural changes are determined for the variants based on the various changes of to the positions of the parent amino acids, interactions between different positions can also be determined. To illustrate, a change at one position of a parent protein can result in a modification to a structural feature at a different position.

As the interactions between positions of the sequence of the parent protein are identified, probability maps can be generated that indicate a probability that a change at a particular position can cause a change in the structural property at a different position. The probability maps can be utilized to predict more complex interactions between changes to positions of the parent protein. For example, interactions between amino acids at multiple positions, such as interactions between a single position and two other positions, interactions between a single position and three other positions, interactions between a single interaction and four other positions, and so forth can be determined based on the probability maps. The variants utilized to produce the structural features models 204 can then be selected based on the probability that a change at the position can have an impact with respect to the structural property. In this way, computational techniques do not have to be utilized where changes to each position of a parent protein for each amino acid that can be substituted at that position do not have to be explicitly determined with respect to 2, 3, 4, or more other positions. Thus, the computation resources utilized to determine the variants of the reference proteins 202 that can be utilized to determine the structural features models 204 are greatly reduced because using conventional techniques to test changes to each position of the reference proteins 202 with respect to various combinations of multiple other positions of the proteins increases exponentially as the number of other positions increases.

Figure 3:
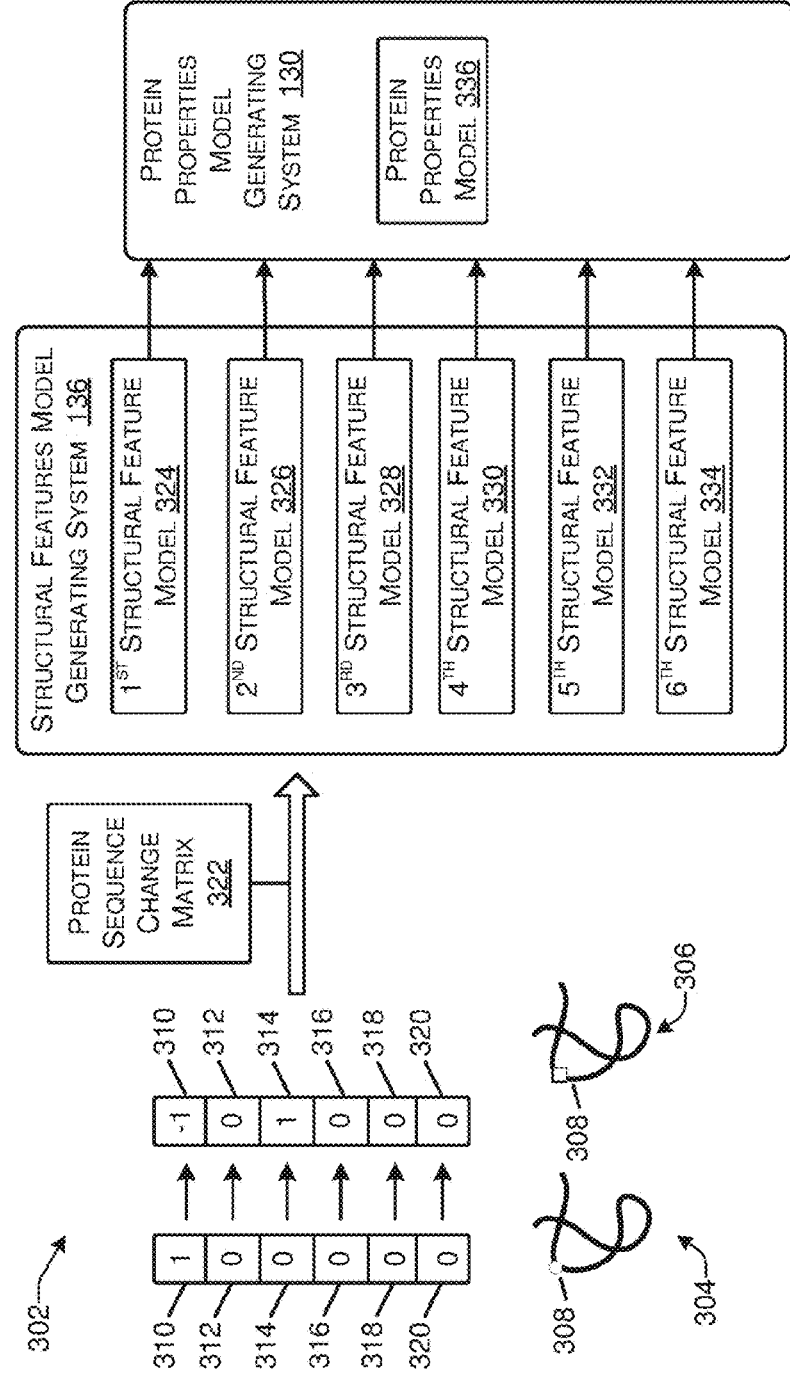
FIG. 3 is a diagram of implementations of an architecture to determine properties of a protein based on changes to structural features of the protein and its variants and changes to sequence of the protein and its variants.

FIG. 3 is a diagram of implementations of an architecture 300 to determine properties of a protein based on changes to structural features of the protein and its variants and changes to sequences of the protein and its variants. The architecture 300 can include an encoding 302 that indicates differences between a protein 304 and a variant 306 of the protein 304. The protein 304 and the variant 306 can vary at a position 308. That is, an amino acid of the protein 304 at the position 308 can be different from an amino acid of the variant 306 at the position 308. The encoding 302 can classify the amino acids that can be associated with each position of the protein 304 and the variant 306. In implementations, the encoding 302 can include a value for each amino acid that can be included at the positions of the protein 304 and the variant 306. In these implementations, the encoding 302 can include twenty-one values for each position of the protein 304 and the variant 306. In other implementations, the encoding 302 can include a value for groups of amino acids that can be associated with each position of the protein 304 and the variant 306. In particular implementations, amino acids can be grouped according to categories, such as acidic, basic, hydrophobic, aromatic, neutral, and deletion. In these implementations, the encoding 302 can include six values for each position of the protein 304 and the variant 306. In additional implementations, amino acids can be grouped according to categories, such as hydrophobic, polar, charged, or deletion. In these scenarios, the encoding can include four values for each position of the protein and the variant 306.

In the illustrative example of FIG. 3, amino acids of the protein 304 and the variant 306 are associated with six categories and the encoding 302 corresponds to the position 308 of the protein 304 and the variant 306. The encoding 302 of the protein 304 and the variant 306 at position 308 can include a first value 310, a second value 312, a third value 314, a fourth value 316, a fifth value 318, and a sixth value 320. In the illustrative example of FIG. 3, the encoding 302 indicates that the position 308 of the protein 304 has a value of 1 for the first value 310 and a value of 0 for the values 312, 314, 316, 318 and 320 indicating that position 308 has an amino acid associated with a category that corresponds to the first value 310. Additionally, the encoding indicates that the position 308 has been changed with respect to the variant 306. In particular, the encoding 302 indicates that the first value 310 for the variant 306 is −1, the third value 314 for the variant 306 is 1 and the values 312, 316, 318, 320 are 0. Thus, in this example the variant 306 does not include an amino acid at position 308 associated with the category indicated by the first value 310, but includes an amino acid at position 308 associated with the category indicated by the third value 314. Further, the value −1 indicates that an amino acid associated with the category that corresponds to the first value 310 has been modified with respect to the variant 306.

Individual encodings for each of the positions of the protein 304 and the variant 306 can be used to generate a protein sequence change matrix 322. The protein sequence change matrix 322 can be provided to the structural features model generating system 136. The structural features model generating system 136 can utilize the protein sequence change matrix 322 and a number of other protein sequence change matrices for additional variants of the protein 304 and also for additional proteins and their variants to produce a number of structural features models. For example, the structural features model generating system 136 can utilize the protein sequence change matrix 322 to generate a first structural feature model 324, a second structural feature model 326, a third structural feature model 328, a fourth structural feature model 330, a fifth structural feature model 332, and a sixth structural feature model 334.

Output generated by the structural features models 324, 326, 328, 330, 332, 334 can be provided to the protein properties model generating system 130 to generate a protein properties model 336. The protein properties model 336 can determine values of a biophysical property of proteins or changes to a biophysical property of proteins with respect to biophysical properties of variants of the proteins. In the illustrative example of FIG. 3, the biophysical property associated with the protein properties model 336 is related to structural properties that correspond to each of the structural features models 324, 326, 328, 330, 332, 334. That is, the structural features associated with the structural features models 324, 326, 328, 330, 332, 334 can be utilized to determine the biophysical property related to the protein properties model 338. The output provided by the structural features models 324, 326, 328, 330, 332, 334 can indicate differences between structural features for proteins and variants of the proteins, such as the protein 304 and the variant 306. In some cases, the differences between structural features for proteins and variants of the proteins can be expressed as differences in a number of positions of the proteins and their variants that have a particular structural feature, such as a number of positions of a variant protein that are hydrophobic with respect to the number of hydrophobic amino acid positions of the parent protein. In other examples, the differences between structural features for proteins and variants of the proteins can be expressed as differences in locations of certain structural features, such as a shift in a turn or sheet of a variant protein with respect to its parent or a shift in location of a hydrophobic group of amino acids of a variant protein with respect to its parent. In various implementations, the protein properties model 338 can determine differences in biophysical properties for proteins and their variants based on the changes in the structural features of the proteins and the variants that are provided by the structural features models 324, 326, 328, 330, 332, 334.

In an illustrative example, the first structural feature model 324 can correspond to hydrophobicity of proteins in a heavy chain of an antibody as measured by a number of positions of the heavy chains of the antibody that include hydrophobic amino acids or as measured by a number of hydrophobic regions of the heavy chains of the antibody. Additionally, the second structural feature model 326 can correspond to a number of positions of the heavy chains of the antibody that include polar amino acid or to a number of polar regions of the heavy chain of the antibody. Further, the third structural features model 328 can correspond to a number of positions of the heavy chains of the antibody that include charged amino acids or to a number of charged regions of the heavy chain of the antibody. The fourth structural feature model 330 can correspond to hydrophobicity of proteins in a light chain of an antibody as measured by a number of positions of the proteins that include hydrophobic amino acids or as measured by a number of hydrophobic regions of the protein light chain of an antibody. In addition, the fifth structural feature model 332 can correspond to a number of positions of the light chains of an antibody that include a polar amino acid or to a number of polar regions of the light chain of the antibody. Also, the sixth structural features model 334 can correspond to a number of positions of light chains of an antibody that include charged amino acids or to a number of charged regions of the light chain of the antibody. Furthermore, the protein properties model 336 can correspond to the temperature at which a protein unfolds, which can be determined based on the structural features associated with the structural features models 324, 326, 328, 330, 332, 334.

Figure 5:
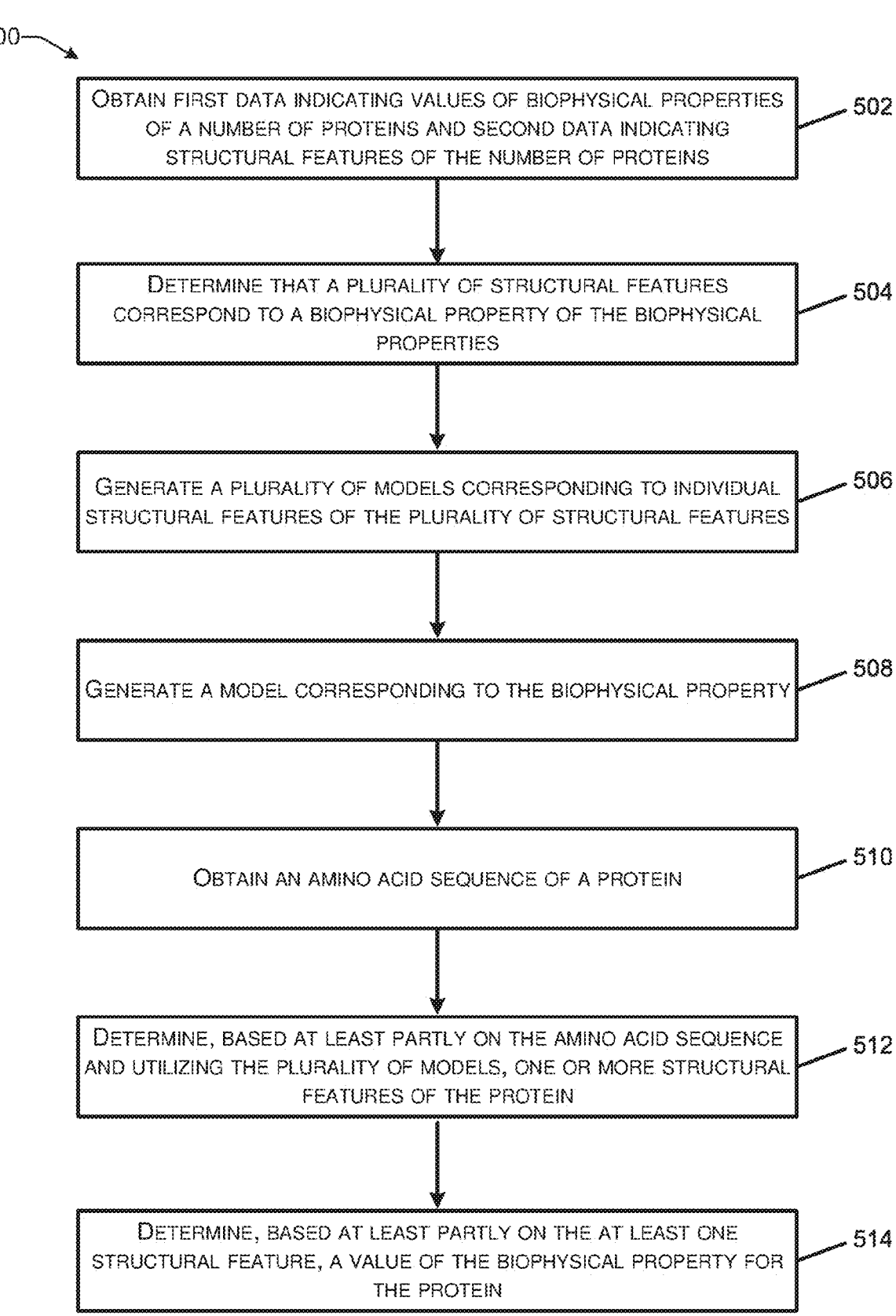
FIG. 5 is a flow diagram of a second example process to generate a plurality of models to determine structural features of proteins for each model to determine values of biophysical properties of proteins.

FIGS. 4 and 5 illustrate example processes of generating models to determine structural features and values of biophysical properties of proteins. These processes (as well as each process described herein) are illustrated as logical flow graphs, each operation of which represents a sequence of operations that can, at least in part, be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the process.

FIG. 4 is a flow diagram of a first example process 400 to generate a first model to predict structural features of a protein based on amino acid sequence and to generate a second model to predict values of biophysical properties of the protein based on the structural features of the protein. At 402, the process 400 includes generating a first model to determine at least one structural feature of proteins based at least partly on amino acid sequences of the proteins.

At 404, the process 400 includes generating a second model to determine at least one biophysical property of the proteins based at least partly on the at least one structural feature of the protein. In addition, at 406, the process 400 includes obtaining an amino acid sequence of a protein.

At 408, the process 400 includes determining, based at least partly on the amino acid sequence of the protein and utilizing the first model, a structural feature of the protein. In some implementations, differences between the amino acid sequence of the protein and an amino acid sequence of a variant of the protein can be determined and the differences can be used by the first model to determine additional differences between the structural feature with respect to the protein and the variant of the protein.

At 410, the process 400 includes determining, based at least partly on the structural feature and utilizing the second model, a value of a biophysical property of the protein. In various implementations, the additional differences between the structural feature with respect to the protein and the variant of the protein can be provided to the second model and the second model can be used to determine, based at least partly on the additional differences between the structural feature with respect to the protein and the variant of the protein, a difference between the biophysical property for the protein and the variant of the protein.

The first model and the second model are generating based at least partly on training data. The training data can include structural features of a plurality of proteins and variants of individual proteins of the plurality of proteins and biophysical properties of the plurality of proteins and the variants of the individual proteins of the plurality of proteins. Additionally, the training data can be analyzed to determine relationships between a plurality of structural features and a biophysical property. In particular implementations, the value of the value of the biophysical property can be determined based on output from a plurality of models with individual models of the plurality of models corresponding to an individual structural feature of the plurality of structural features. In illustrative examples, structural features of proteins can be determined using a combination of a k-Nearest Neighbors model coupled with a neural network and values of biophysical properties of the protein can be determined using a factor-based model.

FIG. 5 is a flow diagram of a second example process 500 to generate a plurality of models to determine structural features of proteins for each model to determine values of biophysical properties of proteins. At 502, the process 500 can include obtaining first data indicating values of biophysical properties of a number of proteins and second data indicating structural features of the number of proteins. In various implementations, the first data and the second data can be obtained from one or more data stores. The data stores can include one or more public databases, in some situations. Additionally, the first data and the second data can be obtained by performing various analytical tests and/or assays with respect to the number of proteins.

At 504, the process 500 can include determining that a plurality of the structural features correspond to a biophysical property of the biophysical properties. In various implementations, the relationships between the plurality of structural features and the biophysical property can be identified through pre-existing research. In other situations, an analysis of the first data and the second data using one or more machine learning techniques can be used to determine the relationships between the plurality of structural features and the biophysical property. Additionally, different biophysical properties can be associated with different groups of structural features. In various implementations, an additional plurality of structural features can be determined to correspond with an additional biophysical property of the biophysical properties with the additional plurality of structural features including at least one structural feature that is different from the plurality of structural features and the additional biophysical property is different from the biophysical property. In an illustrative example, the biophysical property can be a temperature at which the protein unfolds and the plurality of structural features can include a number of polar regions of the protein and a number of hydrophobic regions of the protein.

At 506, the process 500 can include generating a plurality of models corresponding to individual structural features of the plurality of structural features, the plurality of models to predict a presence or an absence of the individual structural features with respect to proteins. At 508, the process 500 can include generating a model corresponding to the biophysical property, the model to predict values for the biophysical property with respect to proteins.

The various models can be trained and tested using an iterative process that selects different groups of proteins and utilizes the structural features and values of biophysical properties of the different groups of proteins to minimize error in the models. In particular implementations, a procedure to train and test models can include determining a first set of proteins from among a group of proteins to train a first model to predict an additional biophysical property of proteins and to train a second model to predict a structural feature of proteins. Additionally, the procedure to train and test models can include training, based at least partly on first amino acid sequences and biophysical properties of the first set of proteins, the first model by determining one or more first equations that include a first plurality of variables and a first plurality of weights and training, based at least partly on the first amino acid sequences and structural features of the first set of proteins, the second model by determining one or more second equations that include a second plurality of variables and a second plurality of weights.

Further, a second set of proteins from among the group of proteins can be determined to test the first model and to test the second model, the second set of proteins having second amino acid sequences. Testing the first model can include determining, based on the second amino acid sequences and utilizing the first model, first values of biophysical properties of the second set of proteins; and determining first differences between the first values of the biophysical properties and second values of the biophysical properties included in data corresponding to the second set of proteins. Testing of the second model can include determining, based on the second amino acid sequences and utilizing the second model, first structural features of the second set of proteins; and determining second differences between the first structural features and second structural features included in the data corresponding to the second set of proteins. In addition, a first amount of error with respect to the first model can be determined based on the first differences; and a second amount of error with respect to the second model can be determined based on the second differences.

An additional iteration of the procedure to train and test the models can include determining a third set of proteins from among the group of proteins to train the first model to predict an additional biophysical property of proteins and to train the second model to predict a structural feature of proteins, wherein the third set of proteins is different from the first set of proteins and the second set of proteins. In addition, the training and testing of the models can include modifying, based at least partly on third amino acid sequences and additional biophysical properties of the third set of proteins, the first model by modifying at least one of the first plurality of variables or the first plurality of weights to produce a modified second model and modifying, based at least partly on the third amino acid sequences and additional structural features of the third set of proteins, the second model by modifying at least one of the second plurality of variables or the second plurality of weights to produce a modified second model. Further, a fourth set of proteins can be determined from among the group of proteins to test the modified first model and to test the modified second model, the fourth set of proteins having fourth amino acid sequences and being different from the first set of proteins, the second set of proteins, and the third set of proteins.

Testing the first modified model can include determining, based on the fourth amino acid sequences and utilizing the first modified model, third values of biophysical properties of the fourth set of proteins and determining third differences between the third values of the biophysical properties and fourth values of the biophysical properties included in data corresponding to the fourth set of proteins. Also, testing the second modified model can include determining, based on the fourth amino acid sequences and utilizing the second modified model, third structural features of the fourth set of proteins and determining fourth differences between the third structural features and fourth structural features included in the data corresponding to the fourth set of proteins. The testing and training procedure can continue by determining that a third amount of error is less than the first amount of error based at least partly the third differences being less than the first differences; and determining that a fourth amount of error is less than the second amount of error based at least partly on the fourth differences being less than the second differences.

At 510, the process 500 can include obtaining an amino acid sequence of a protein and at 512, the process 500 can include determining, based at least partly on the amino acid sequence and utilizing the plurality of models, one or more structural features of the protein, wherein at least one structural feature of the one or more structural features is included in the plurality of structural features. Further, at 514, the process 500 can include determining, based at least partly on the at least one structural feature and utilizing the model, a value of the biophysical property for the protein.

Figure 6:
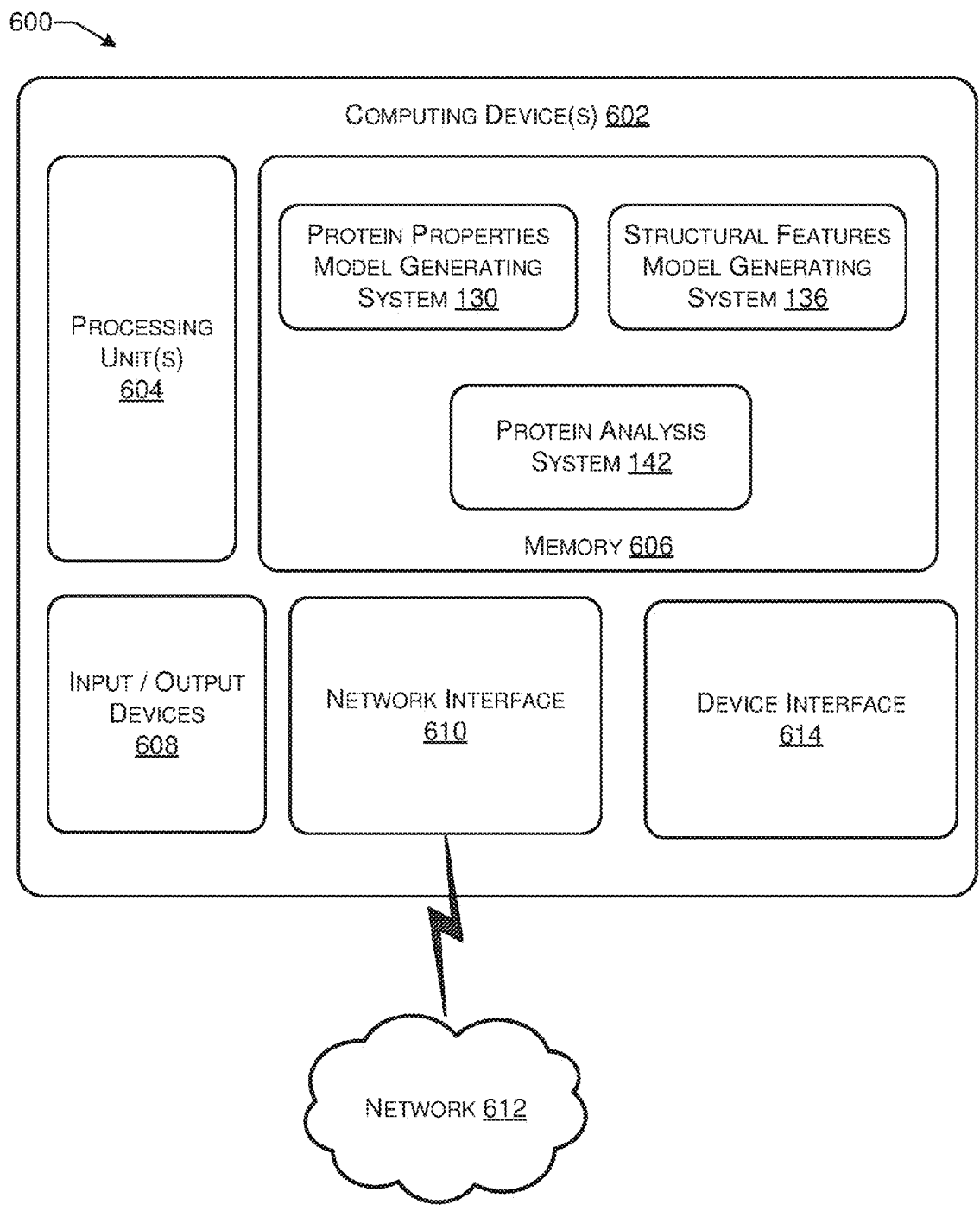
FIG. 6 shows a block diagram of an example system including one or more computing devices to generate and implement models to determine structural features and values of biophysical properties of proteins.

FIG. 6 shows a block diagram of an example system 600 including one or more computing devices 602 to generate and implement models to determine structural features and values of biophysical properties of proteins. The computing device 602 can be implemented with one or more processing unit(s) 604 and memory 606, both of which can be distributed across one or more physical or logical locations. For example, in some implementations, the operations described as being performed by the computing device(s) 602 can be performed by multiple computing devices. In some cases, the operations described as being performed by the computing device(s) 602 can be performed in a cloud computing architecture.

The processing unit(s) 604 can include any combination of central processing units (CPUs), graphical processing units (GPUs), single core processors, multi-core processors, application-specific integrated circuits (ASICs), programmable circuits such as Field Programmable Gate Arrays (FPGA), and the like. In one implementation, one or more of the processing units(s) 604 can use Single Instruction Multiple Data (SIMD) parallel architecture. For example, the processing unit(s) 604 can include one or more GPUs that implement SIMD. One or more of the processing unit(s) 604 can be implemented as hardware devices. In some implementations, one or more of the processing unit(s) 604 can be implemented in software and/or firmware in addition to hardware implementations. Software or firmware implementations of the processing unit(s) 604 can include computer- or machine-executable instructions written in any suitable programming language to perform the various functions described. Software implementations of the processing unit(s) 604 may be stored in whole or part in the memory 606.

Alternatively, or additionally, the functionality of computing device(s) 602 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 606 of the computing device 602 can include removable storage, non-removable storage, local storage, and/or remote storage to provide storage of computer-readable instructions, data structures, program modules, and other data. The memory 606 can be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media can embody computer-readable instructions, data structures, program modules, or other data in a modulated data signal, such as a carrier wave, or other transmission mechanism. As defined herein, computer-readable storage media and communications media are mutually exclusive.

The computing device(s) 602 can include and/or be coupled with one or more input/output devices 608 such as a keyboard, a pointing device, a touchscreen, a microphone, a camera, a display, a speaker, a printer, and the like. Input/output devices 708 that are physically remote from the processing unit(s) 604 and the memory 606 can also be included within the scope of the input/output devices 608.

Also, the computing device(s) 602 can include a network interface 610. The network interface 610 can be a point of interconnection between the computing device(s) 602 and one or more networks 612. The network interface 610 can be implemented in hardware, for example, as a network interface card (NIC), a network adapter, a LAN adapter or physical network interface. The network interface 610 can be implemented in software. The network interface 610 can be implemented as an expansion card or as part of a motherboard. The network interface 610 can implement electronic circuitry to communicate using a specific physical layer and data link layer standard, such as Ethernet or Wi-Fi. The network interface 610 can support wired and/or wireless communication. The network interface 610 can provide a base for a full network protocol stack, allowing communication among groups of computers on the same local area network (LAN) and large-scale network communications through routable protocols, such as Internet Protocol (IP).

The one or more networks 612 can include any type of communications network, such as a local area network, a wide area network, a mesh network, an ad hoc network, a peer-to-peer network, the Internet, a cable network, a telephone network, a wired network, a wireless network, combinations thereof, and the like.

A device interface 614 can be part of the computing device(s) 602 that provides hardware to establish communicative connections to other devices. The device interface 614 can also include software that supports the hardware. The device interface 614 can be implemented as a wired or wireless connection that does not cross a network. A wired connection may include one or more wires or cables physically connecting the computing device(s) 602 to another device. The wired connection can be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like.

The computing device(s) 602 can include multiple systems and/or modules that may be implemented as instructions stored in the memory 606 for execution by processing unit(s) 604 and/or implemented, in whole or in part, by one or more hardware logic components or firmware. The memory 606 can be used to store any number of functional components that are executable by the one or more processors processing units 604. In many implementations, these functional components comprise instructions or programs that are executable by the one or more processing units 604 and that, when executed, implement operational logic for performing the operations attributed to the computing device(s) 602. Functional components of the computing device 602 that can be executed on the one or more processing units 604 for implementing the various functions and features related to generating and implementing models to determine structural features and values of biophysical properties, as described herein, include the protein properties model generating system 130, the structural features model generating system 136, and the protein analysis system 142. One or more of the systems 130, 136, and 142 can be used to implement architectures 100, 200, 300 and processes 400 and 500 of FIG. 1, FIG. 2, FIG. 3, FIG. 4, and FIG. 5.

In particular implementations, the protein properties model generating system 130 can include computer-readable instructions that are executable by the one or more processing units 604 to generate models to predict values of biophysical properties of proteins. The models can be generated using training data that includes values of biophysical properties of a number of proteins and variants of the number of proteins. Additionally, the structural features model generating system 136 can include computer-readable instructions that are executable by the one or more processing units 604 to analyze training data to generate models to predict structural features of proteins based on amino acid sequences of the proteins. The training data can also include structural features of the proteins and their variants included in the training data. The protein properties model generating system 130 and the structural features model generating system 136 can work separately, or in conjunction with one another, to train and test the models to predict values of biophysical properties of proteins and structural features of proteins. The training data can be derived from assays and/or analytical tests performed on the proteins included in the training data set.

In various implementations, protein analysis system 142 can implement the models generated by the protein properties model generating system 130 and the structural features model generating system 136 to predict values of biophysical properties of proteins and structural features of proteins that have not been expressed and analyzed according to one or more assays or analytical techniques. The protein analysis system 142 can utilize models generated by the structural features model generating system 136 to predict structural features of proteins based on the amino acid sequence of the proteins. In addition, the protein analysis system 142 can utilize models generated by the protein properties model generating system 130 to predict values of biophysical properties of proteins based at least partly on the structural features of the proteins and/or the amino acid sequences of the proteins.

In additional implementations, the structural features model generating system 136 can generate models for individual amino acids in an amino acid sequence of a protein. For example, the structural features model generating system 136 can generate models to predict whether an amino acid at a particular position of a protein has and/or participates in one or more structural features of the protein. The structural features related to the amino acid can include hydrophobic, polar, aromatic, acidic, basic, deletion, and/or neutral, among others. In certain implementations, the structural features model generating system 136 can generate a model for an individual amino acid of a protein. Additionally, the structural features model generating system 136 can generate models for every amino acid in a sequence of amino acids of a protein to predict whether the individual amino acids have and/or participate in one or more structural features. In particular implementations, individual models can be generated for individual structural features of individual amino acids of a protein. To illustrate, a model can be determined to predict charge of an amino acid of a protein.

In various implementations, a training data set can comprise a subset of variants for individual amino acids of a protein. The subset of variants can be determined based on a likelihood of interaction between a candidate amino acid for which a model is being generated and other amino acids of the protein. The likelihood of interaction between a candidate amino acid and other amino acids can be determined by analyzing data associated with the amino acid and other amino acids of the protein. In some examples, the data being analyzed can be related to proximity of amino acids with respect to the candidate amino acid, atoms included in the candidate amino acid and atoms included in additional amino acids of the protein, and/or other properties of the candidate amino acid in relation to additional amino acids included in the protein (e.g., aromatic, acidic, basic, etc.). In an illustrative example, a likelihood that a candidate amino acid would interact with additional amino acids of a protein can be based on a probability being above a threshold probability that at least one atom of the candidate amino acid would interact with another atom of an additional amino acid of the protein.

After determining one or more additional amino acids of a protein that have at least a threshold probability of interacting with a candidate amino acid, the structural features model generating system 136 can determine mutations of the one or more additional amino acids. The structural features model generating system 136 can then determine whether or not the mutations have an effect on one or more structural features related to the candidate amino acid. In some situations, the structural features model generating system 136 can determine whether or not mutations have an effect by analyzing data corresponding to the candidate amino acid and data corresponding to the various mutated amino acids. The data can be related to the types of atoms included in the candidate amino acid with respect to the atoms of the mutated amino acids. The data analyzed can also include information obtained from analytical tests and/or assays performed with respect to the mutations of the protein in relation to the non-mutated protein. By training the models for individual amino acids of a protein on a data set that includes amino acids that have at least a threshold probability of interacting with a candidate amino acid, the models can be more accurate because the data set is not as sparse as in situations where a candidate amino acid was analyzed with respect to every possible mutation of every amino acid of a protein In particular, if every mutation of every amino acid of a protein was analyzed to determine whether the mutation had an effect on a structural feature of the candidate amino acid, the number of additional amino acids and mutations having greater than a threshold effect would be relatively small in relation to the number of amino acids and their mutations that have at least a threshold effect on the structural feature when selected from a group of amino acids that has greater than a threshold probability of interacting with the candidate amino acid.

Further, the structural features model generating system 136 can utilize particular encodings to generate models to predict structural features for candidate amino acids. In a particular example, each amino acid can be encoded for various structural features, such as hydrophobicity, polar, charged, and/or deletion. Mutations for the candidate amino acid can also be encoded in a similar manner. In situations, where the structural features model generating system 136 obtains input in the form of differences in structural features between an amino acid and a variant of the amino acid, information can be lost because the difference in the amino acid sequence of the protein that includes the candidate amino acid and the encoding of the amino acid sequence that includes the variant can indicate only the changes to the structural property of the mutation and not the rest of the encoding of the other amino acids. To compensate for this loss of information, the structural features model generating system 136 can multiply the difference in the amino acid sequence of the protein with the candidate amino acid and the amino acid sequence of the protein with a mutation at the same position by two and then subtract the amino acid sequence of the variant. In this way, the encoding of the amino acids at other positions is preserved and the modification at the mutated position of the variant is also captured. In this way, the accuracy of the models generated by the structural features model generating system 136 can be improved.

Figure 7:
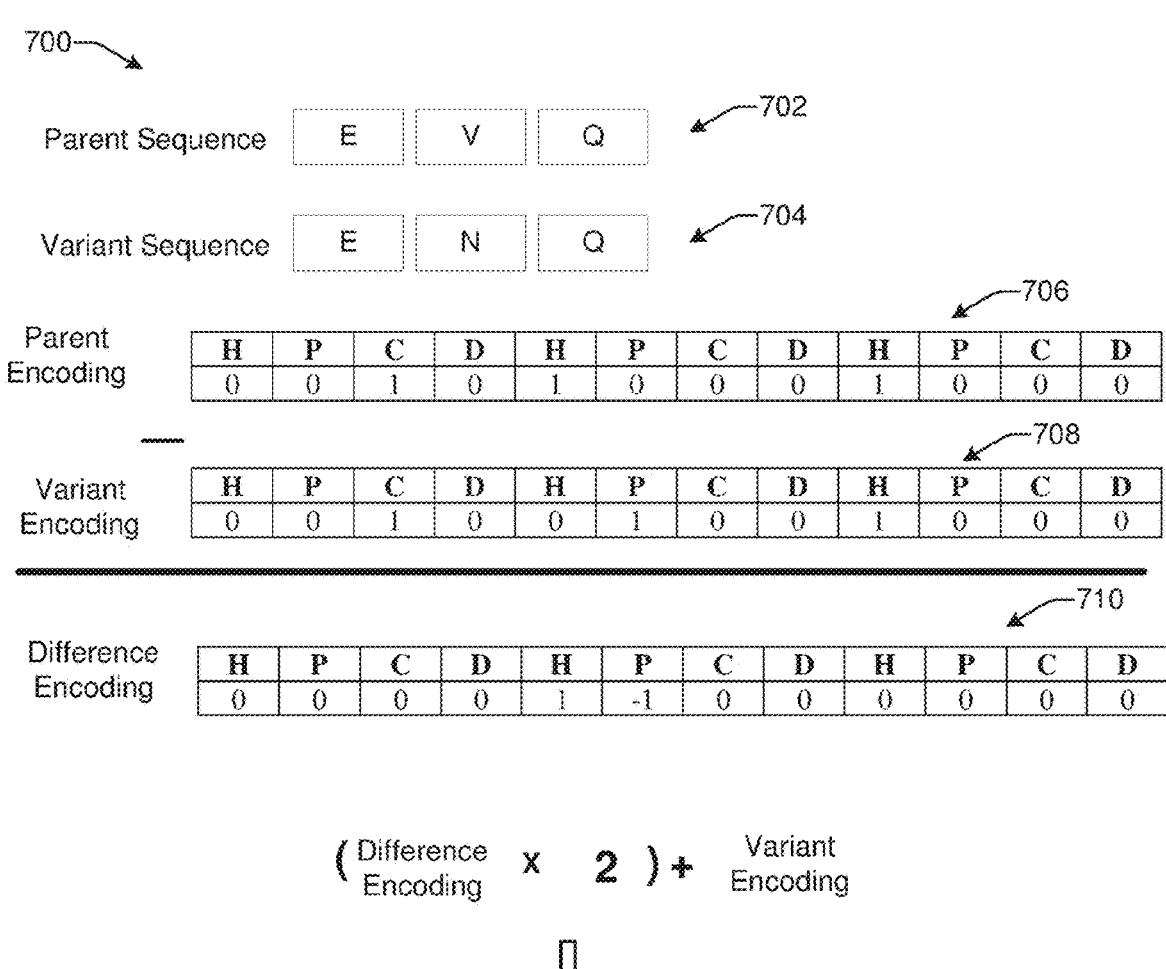
FIG. 7 illustrates an example encoding for a base protein and a variant of the base protein.

An example of the encodings described above is shown in FIG. 7. In particular, the illustrative example of FIG. 7 includes a portion of a parent protein amino acid sequence 702 and a portion of a variant protein amino acid sequence 704 where the valine of the parent protein amino acid sequence 702 is changed to an asparagine. A first encoding, referred to as the "parent encoding", 706 corresponds to an encoding of the parent protein amino acid sequence 702 and a second encoding 708, referred to as the "variant encoding", corresponds to an encoding of the variant protein amino acid sequence 704. A third encoding 710 is produced by taking the difference between the first encoding and the second encoding. Additionally, a fourth encoding 712 that corresponds to an encoding utilized by the structural features model generating system 136 can be produced by multiplying the third encoding 710 by 2 and then adding the variant encoding 708.

EXAMPLE IMPLEMENTATIONS

Clause 1. A method comprising: generating a first model to determine at least one structural feature of proteins based at least partly on amino acid sequences of the proteins; generating a second model to determine at least one biophysical property of the proteins based at least partly on the at least one structural feature of the proteins; obtaining an amino acid sequence of a protein; determining, based at least partly on the amino acid sequence of the protein and utilizing the first model, a structural feature of the protein; and determining, based at least partly on the structural feature and utilizing the second model, a value of a biophysical property of the protein.

Clause 2. The method of clause 1, further comprising: determining differences between the amino acid sequence of the protein and an amino acid sequence of a variant of the protein: and providing the differences between the amino acid sequences to the first model to determine additional differences between the structural feature with respect to the protein and the variant of the protein.

Clause 3. The method of clause 2, further comprising: providing the additional differences between the structural feature with respect to the protein and the variant of the protein to the second model; and determining, based at least partly on the additional differences between the structural feature with respect to the protein and the variant of the protein, a difference between the biophysical property for the protein and the variant of the protein.

Clause 4. The method of any one of clauses 1-3, wherein the first model and the second model are generating based at least partly on training data and the training data includes structural features of a plurality of proteins and variants of individual proteins of the plurality of proteins and biophysical properties of the plurality of proteins and the variants of the individual proteins of the plurality of proteins.

Clause 5. The method of any one of clauses 1-4, wherein the structural feature of the protein is determined using a combination of a k-Nearest Neighbors model coupled with a neural network and the value of the biophysical property of the protein is determined using a factor-based model.

Clause 6. The method of any one of clauses 1-5, further comprising analyzing the training data to determine relationships between a plurality of structural features and a biophysical property, and wherein the value of the value of the biophysical property is determined based on output from a plurality of models, individual models of the plurality of models corresponding to an individual structure feature of the plurality of structural features.

Clause 7. A method comprising: obtaining first data indicating values of biophysical properties of a number of proteins and second data indicating structural features of the number of proteins; determining that a plurality of the structural features correspond to a biophysical property of the biophysical properties; generating a plurality of models corresponding to individual structural features of the plurality of structural features, the plurality of models to predict a presence or an absence of the individual structural features with respect to proteins; generating a model corresponding to the biophysical property, the model to predict values for the biophysical property with respect to proteins; obtaining an amino acid sequence of a protein; determining, based at least partly on the amino acid sequence and utilizing the plurality of models, one or more structural features of the protein, wherein at least one structural feature of the one or more structural features is included in the plurality of structural features; and determining, based at least partly on the at least one structural feature and utilizing the model, a value of the biophysical property for the protein.

Clause 8. The method of clause 7, further comprising: determining that an additional plurality of structural features correspond to an additional biophysical property of the biophysical properties, wherein the additional plurality of structural features includes at least one structural feature that is different from the plurality of structural features and the additional biophysical property is different from the biophysical property.

Clause 9. The method of clause 8, wherein the biophysical property is a temperature at which the protein unfolds and the plurality of structural features includes a number of polar regions of the protein and a number of hydrophobic regions of the protein.

Clause 10. The method of clause 7, further comprising: determining a first set of proteins from among a group of proteins to train a first model to predict an additional biophysical property of proteins and to train a second model to predict a structural feature of proteins; training, based at least partly on first amino acid sequences and biophysical properties of the first set of proteins, the first model by determining one or more first equations that include a first plurality of variables and a first plurality of weights; training, based at least partly on the first amino acid sequences and structural features of the first set of proteins, the second model by determining one or more second equations that include a second plurality of variables and a second plurality of weights; and determining a second set of proteins from among the group of proteins to test the first model and to test the second model, the second set of proteins having second amino acid sequences.

Clause 11. The method of clause 10, further comprising: testing the first model by: determining, based on the second amino acid sequences and utilizing the first model, first values of biophysical properties of the second set of proteins; and determining first differences between the first values of the biophysical properties and second values of the biophysical properties included in data corresponding to the second set of proteins; and testing the second model by: determining, based on the second amino acid sequences and utilizing the second model, first structural features of the second set of proteins; and determining second differences between the first structural features and second structural features included in the data corresponding to the second set of proteins.

Clause 12. The method of clause 11, further comprising: determining a first amount of error with respect to the first model based on the first differences; and determining a second amount of error with respect to the second model based on the second differences.

Clause 13. The method of clause 12, further comprising: determining a third set of proteins from among the group of proteins to train the first model to predict an additional biophysical property of proteins and to train the second model to predict a structural feature of proteins, wherein the third set of proteins is different from the first set of proteins and the second set of proteins; modifying, based at least partly on third amino acid sequences and additional biophysical properties of the third set of proteins, the first model by modifying at least one of the first plurality of variables or the first plurality of weights to produce a modified second model; and modifying, based at least partly on the third amino acid sequences and additional structural features of the third set of proteins, the second model by modifying at least one of the second plurality of variables or the second plurality of weights to produce a modified second model.

Clause 14. The method of clause 13, further comprising: determining a fourth set of proteins from among the group of proteins to test the modified first model and to test the modified second model, the fourth set of proteins having fourth amino acid sequences and being different from the first set of proteins, the second set of proteins, and the third set of proteins; testing the first modified model by: determining, based on the fourth amino acid sequences and utilizing the first modified model, third values of biophysical properties of the fourth set of proteins; and determining third differences between the third values of the biophysical properties and fourth values of the biophysical properties included in data corresponding to the fourth set of proteins; and testing the modified second model by: determining, based on the fourth amino acid sequences and utilizing the second modified model, third structural features of the fourth set of proteins; and determining fourth differences between the third structural features and fourth structural features included in the data corresponding to the fourth set of proteins.

Clause 15. The method of clause 14, further comprising: determining that a third amount of error is less than the first amount of error based at least partly the third differences being less than the first differences; and determining that a fourth amount of error is less than the second amount of error based at least partly on the fourth differences being less than the second differences.

Clause 16. The method of clause 10, wherein the first set of proteins includes at least a first protein and one or more variants of the first protein and the second set of proteins at least a second protein and one or more variants of the second protein.

Clause 17. A method comprising: determining an encoding indicating differences between a base protein and a variant of the base protein; generating, based at least partly on the encoding, a protein sequence change matrix, the protein sequence change matrix indicating, for individual positions of an amino acid sequence of the base protein and corresponding individual positions of an amino acid sequence of the variant, differences between at least one of (i) a first amino acid sequence of the base protein and a second amino acid sequence of the variant or (ii) first structural features of the base protein and second structural features of the variant; generating a plurality of additional protein sequence change matrices for a plurality of additional base proteins and one or more variants of each of the plurality of additional base proteins; generating, based at least partly on the protein sequence change matrix and the plurality of protein sequence change matrices, a plurality of structural features models, individual structural features models of the plurality of structural features models corresponding to an individual structural feature of proteins; generating, based at least partly on output from the plurality of structural features models with respect to the base protein, the plurality of additional base proteins, the variant, and the plurality of variants, a protein properties model; obtaining an amino acid sequence of a protein; determining, based at least partly on the amino acid sequence and utilizing the plurality of structural features models, additional output indicating one or more structural features of the protein; and determining, based at least partly on the one or more structural features and utilizing the protein properties model, a value of a biophysical property of the protein.

Clause 18. The method of clause 17, further comprising: obtaining an additional amino acid sequence of a variant of the protein; and determining, based at least partly on the amino acid sequence of the protein and the additional amino acid sequence of the variant of the protein and utilizing the plurality of structural features models, differences between one or more structural feature of the protein and the variant of the protein.

Clause 19. The method of clause 17 or 18, further comprising: generating a probability map indicating individual probabilities that a change in an amino acid located at an individual position of the amino acid sequence of the protein results in a change in a structural feature of the protein.

Clause 20. The method of clause 19, further comprising: determining at least a portion of the plurality of variants based at least partly on the probability map.

Clause 21. A system comprising: one or more processors; and one or more non-transitory computer-readable media storing computer-readable instructions that, when executed by the one or more processors, perform operations comprising: generating a first model to determine at least one structural feature of proteins based at least partly on amino acid sequences of the proteins; generating a second model to determine at least one biophysical property of the proteins based at least partly on the at least one structural feature of the proteins; obtaining an amino acid sequence of a protein; determining, based at least partly on the amino acid sequence of the protein and utilizing the first model, a structural feature of the protein; and determining, based at least partly on the structural feature and utilizing the second model, a value of a biophysical property of the protein.

Clause 22. The system of clause 21, wherein the operations further comprise: determining differences between the amino acid sequence of the protein and an amino acid sequence of a variant of the protein: and providing the differences between the amino acid sequences to the first model to determine additional differences between the structural feature with respect to the protein and the variant of the protein.

Clause 23. The system of clause 22, wherein the operations further comprise: providing the additional differences between the structural feature with respect to the protein and the variant of the protein to the second model; and determining, based at least partly on the additional differences between the structural feature with respect to the protein and the variant of the protein, a difference between the biophysical property for the protein and the variant of the protein.

Clause 24. The system of any one of clauses 21-23, wherein the first model and the second model are generating based at least partly on training data and the training data includes structural features of a plurality of proteins and variants of individual proteins of the plurality of proteins and biophysical properties of the plurality of proteins and the variants of the individual proteins of the plurality of proteins.

Clause 25. The system of any one of clauses 21-24, wherein the structural feature of the protein is determined using a combination of a k-Nearest Neighbors model coupled with a neural network and the value of the biophysical property of the protein is determined using a factor-based model.

Clause 26. The system of any one of clauses 21-25, wherein the operations further comprise analyzing the training data to determine relationships between a plurality of structural features and a biophysical property, and wherein the value of the value of the bio-physical property is determined based on output from a plurality of models, individual models of the plurality of models corresponding to an individual structure feature of the plurality of structural features.

Clause 27. A system comprising: one or more processors; and one or more non-transitory computer-readable media storing computer-readable instructions that, when executed by the one or more processors, perform operations comprising: obtaining first data indicating values of biophysical properties of a number of proteins and second data indicating structural features of the number of proteins; determining that a plurality of the structural features correspond to a biophysical property of the biophysical properties; generating a plurality of models corresponding to individual structural features of the plurality of structural features, the plurality of models to predict a presence or an absence of the individual structural features with respect to proteins; generating a model corresponding to the biophysical property, the model to predict values for the biophysical property with respect to proteins; obtaining an amino acid sequence of a protein; determining, based at least partly on the amino acid sequence and utilizing the plurality of models, one or more structural features of the protein, wherein at least one structural feature of the one or more structural features is included in the plurality of structural features; and determining, based at least partly on the at least one structural feature and utilizing the model, a value of the biophysical property for the protein.

Clause 28. The system of clause 27, wherein the operations further comprise: determining that an additional plurality of structural features correspond to an additional biophysical property of the biophysical properties, wherein the additional plurality of structural features includes at least one structural feature that is different from the plurality of structural features and the additional biophysical property is different from the biophysical property.

Clause 29. The system of clause 28, wherein the bio-physical property is a temperature at which the protein unfolds and the plurality of structural features includes a number of polar regions of the protein and a number of hydrophobic regions of the protein.

Clause 30. The system of clause 27, wherein the operations further comprise: determining a first set of pro-teins from among a group of proteins to train a first model to predict an additional biophysical property of proteins and to train a second model to predict a structural feature of proteins; training, based at least partly on first amino acid sequences and biophysical properties of the first set of proteins, the first model by determining one or more first equations that include a first plurality of variables and a first plurality of weights; training, based at least partly on the first amino acid sequences and structural features of the first set of proteins, the second model by determining one or more second equations that include a second plurality of variables and a second plurality of weights; and determining a second set of proteins from among the group of proteins to test the first model and to test the second model, the second set of proteins having second amino acid sequences.

Clause 31. The system of clause 30, wherein the opera-tions further comprise: testing the first model by: determining, based on the second amino acid sequences and utilizing the first model, first values of biophysical properties of the second set of proteins; and determin-ing first differences between the first values of the biophysical properties and second values of the bio-physical properties included in data corresponding to the second set of proteins; and testing the second model by: determining, based on the second amino acid sequences and utilizing the second model, first struc-tural features of the second set of proteins; and deter-mining second differences between the first structural features and second structural features included in the data corresponding to the second set of proteins.

Clause 32. The system of clause 31, wherein the opera-tions further comprise: determining a first amount of error with respect to the first model based on the first differences; and determining a second amount of error with respect to the second model based on the second differences.

Clause 33. The system of clause 32, wherein the opera-tions further comprise: determining a third set of pro-teins from among the group of proteins to train the first model to predict an additional biophysical property of proteins and to train the second model to predict a structural feature of proteins, wherein the third set of proteins is different from the first set of proteins and the second set of proteins; modifying, based at least partly on third amino acid sequences and additional biophysi-cal properties of the third set of proteins, the first model by modifying at least one of the first plurality of variables or the first plurality of weights to produce a modified second model; and modifying, based at least partly on the third amino acid sequences and additional structural features of the third set of proteins, the second model by modifying at least one of the second plurality of variables or the second plurality of weights to produce a modified second model.

Clause 34. The system of clause 33, wherein the opera-tions further comprise: determining a fourth set of proteins from among the group of proteins to test the modified first model and to test the modified second model, the fourth set of proteins having fourth amino acid sequences and being different from the first set of proteins, the second set of proteins, and the third set of proteins; testing the first modified model by: determin-ing, based on the fourth amino acid sequences and utilizing the first modified model, third values of bio-physical properties of the fourth set of proteins; and determining third differences between the third values of the biophysical properties and fourth values of the biophysical properties included in data corresponding to the fourth set of proteins; and testing the modified second model by: determining, based on the fourth amino acid sequences and utilizing the second modified model, third structural features of the fourth set of proteins; and determining fourth differences between the third structural features and fourth structural fea-tures included in the data corresponding to the fourth set of proteins.

Clause 35. The system of clause 34, wherein the opera-tions further comprise: determining that a third amount of error is less than the first amount of error based at least partly the third differences being less than the first differences; and determining that a fourth amount of error is less than the second amount of error based at least partly on the fourth differences being less than the second differences.

Clause 36. The system of clause 30, wherein the first set of proteins includes at least a first protein and one or more variants of the first protein and the second set of proteins at least a second protein and one or more variants of the second protein.

Clause 37. A system comprising: one or more processors; and one or more non-transitory computer-readable media storing computer-readable instructions that, when executed by the one or more processors, perform operations comprising: determining an encoding indicating differences between a base protein and a variant of the base protein; generating, based at least partly on the encoding, a protein sequence change matrix, the protein sequence change matrix indicating, for individual positions of an amino acid sequence of the base protein and corresponding individual positions of an amino acid sequence of the variant, differences between at least one of (i) a first amino acid sequence of the base protein and a second amino acid sequence of the variant or (ii) first structural features of the base protein and second structural features of the variant; generating a plurality of additional protein sequence change matrices for a plurality of additional base proteins and one or more variants of each of the plurality of additional base proteins; generating, based at least partly on the protein sequence change matrix and the plurality of protein sequence change matrices, a plurality of structural features models, individual structural features models of the plurality of structural features models corresponding to an individual structural feature of proteins; generating, based at least partly on output from the plurality of structural features models with respect to the base protein, the plurality of additional base proteins, the variant, and the plurality of variants, a protein properties model; obtaining an amino acid sequence of a protein; determining, based at least partly on the amino acid sequence and utilizing the plurality of structural features models, additional output indicating one or more structural features of the protein; and determining, based at least partly on the one or more structural features and utilizing the protein properties model, a value of a biophysical property of the protein.

Clause 38. The system of clause 37, wherein the operations further comprise: obtaining an additional amino acid sequence of a variant of the protein; and determining, based at least partly on the amino acid sequence of the protein and the additional amino acid sequence of the variant of the protein and utilizing the plurality of structural features models, differences between one or more structural feature of the protein and the variant of the protein.

Clause 39. The system of clause 17 or 18, wherein the operations further comprise: generating a probability map indicating individual probabilities that a change in an amino acid located at an individual position of the amino acid sequence of the protein results in a change in a structural feature of the protein.

Clause 40. The system of clause 19, wherein the operations further comprise: determining at least a portion of the plurality of variants based at least partly on the probability map.

EXPERIMENTAL EXAMPLES

Figure 8:
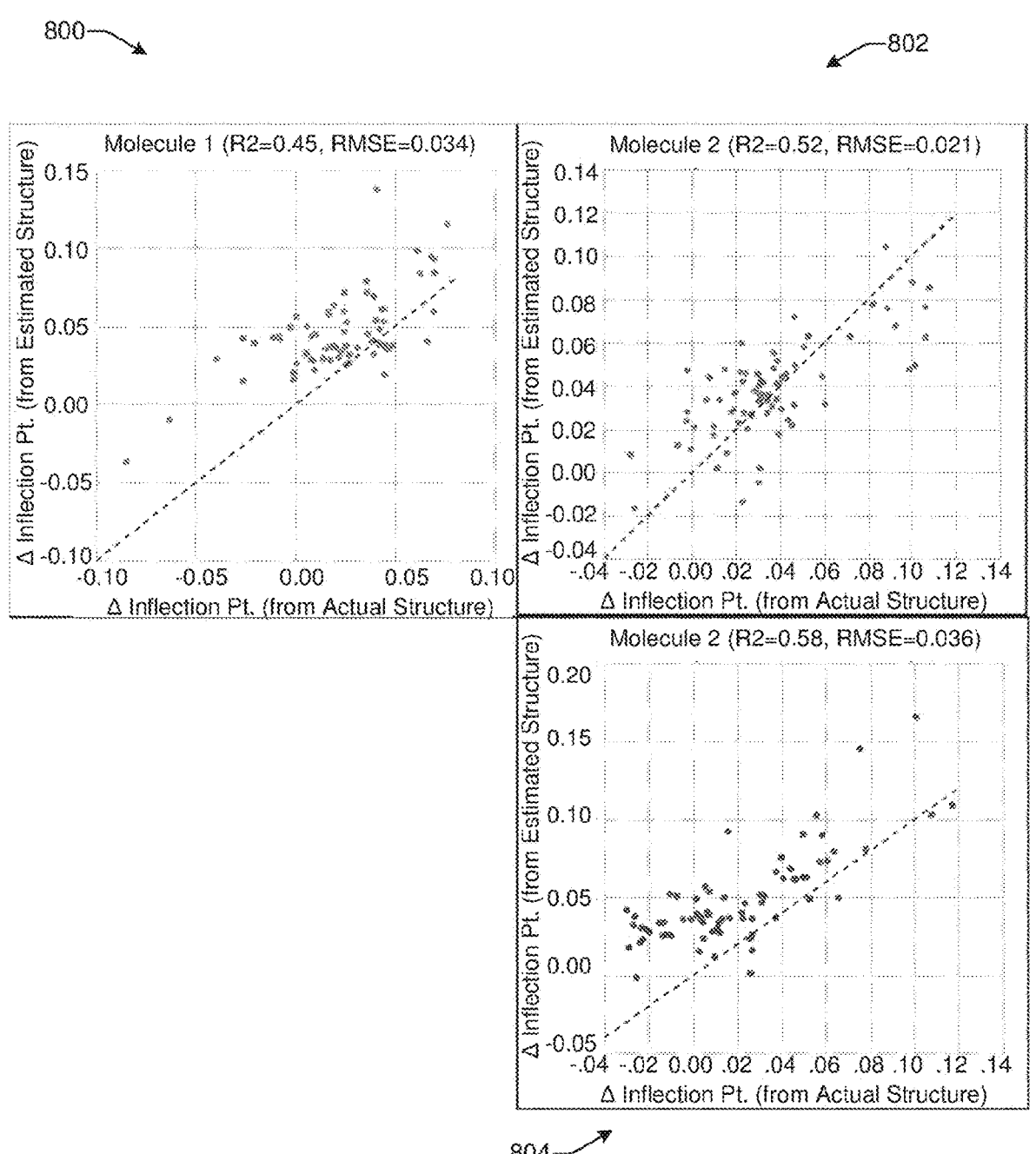
FIG. 8 illustrates a first plot, a second plot, and a third plot showing changes in how a protein unfolds with various concentrations of chemical denaturant (i.e., inflection point) for proteins and variants of the proteins.

FIG. 8 illustrates a first plot 800, a second plot 802, and a third plot 804 showing changes in how a protein unfolds with various concentrations of chemical denaturant (i.e., inflection point) for proteins and variants of the proteins. The x-axis of plots 800, 802, 804 indicate the predicted change in inflection point using a biophysical property model when the inputs to the biophysical property model are determined using the atomic structure of a protein and conventional computational techniques that minimize energy related to the folding of the protein. The y-axis of plots 800, 802, 804 indicate the inflection point changes using the same biophysical property model determined using inputs generated according to implementations described herein where relative changes to sequence are utilized to determine structural features models.

The subject matter described above is provided by way of illustration only and should not be construed as limiting. Furthermore, the claimed subject matter is not limited to implementations that solve any or all disadvantages noted in any part of this disclosure. Various modifications and changes can be made to the subject matter described herein without following the example configurations and applications illustrated and described, and without departing from the true spirit and scope of the present invention, which is set forth in the following claims.

What is claimed is:

1. A method comprising:
performing one or more first analytical procedures to determine amino acid sequences of a plurality of immunoglobin (Ig) antibodies and a plurality of variants for individual Ig antibodies of the plurality of Ig antibodies;
performing one or more second analytical procedures to determine first structural features of the plurality of Ig antibodies and to determine second structural features of the plurality of variants for the individual Ig antibodies;
performing one or more third analytical procedures to determine first values of a plurality of biophysical properties with respect to the plurality of Ig antibodies and to determine second values of the plurality of biophysical properties for the plurality of variants for the individual Ig antibodies;
generating, by one or more computing devices, training data including first data indicating the first values of the plurality of biophysical properties and the second values of the plurality of biophysical properties and second data indicating the first structural features and the second structural features;
generating, by the one or more computing devices, individual encodings between the individual Ig antibodies and the plurality of variants corresponding to the individual Ig antibodies based on (i) differences between amino acid sequences of the individual Ig antibodies and the plurality of variants corresponding to the individual Ig antibodies and (ii) one or more structural features corresponding to individual positions of the amino acid sequences of the individual Ig antibodies and the plurality of variants corresponding to the individual Ig antibodies;

performing, by the one or more computing devices and based on the second data and the individual encodings, a first training process to generate a plurality of first machine learning models corresponding to individual structural features of a plurality of structural features, wherein the plurality of first machine learning models include at least one of a random forests model, or a k-Nearest Neighbor model coupled with a neural network, and individual first machine learning models of the plurality of first machine learning models predict a presence or an absence of an individual structural feature;

performing, by the one or more computing devices and based on the first data, a second training process to generate a plurality of second machine learning models, individual second machine learning models of the plurality of second machine learning models corresponding to an individual biophysical property of the plurality of biophysical properties, the plurality of second machine learning models being different from the plurality of first machine learning models and the individual second machine learning models predict values for the individual biophysical property that corresponds to the individual second machine learning models, wherein the individual second machine learning models include a random forests model or a convolutional neural network;

obtaining, by the one or more computing devices, an amino acid sequence of an Ig antibody, wherein the Ig antibody is not included in the plurality of Ig antibodies or in the plurality of variants of the individual Ig antibodies;

determining, by the one or more computing devices and based on the amino acid sequence and utilizing the plurality of first machine learning models, positions of the Ig antibody that correspond to one or more structural features of the plurality of structural features;

providing, by the one or more computing devices, output from the plurality of first machine learning models as input to an individual second machine learning model that corresponds to a biophysical property of the plurality of biophysical properties, the output of each individual first machine learning model indicating a prediction of a number of positions of the Ig antibody that have the individual structural feature corresponding to the individual first machine learning model; and determining, by the one or more computing devices and based on the output from the plurality of first machine learning models and utilizing the individual second machine learning model, a value of the biophysical property for the Ig antibody.

2. The method of claim 1, further comprising:

determining that an additional plurality of structural features correspond to an additional biophysical property of the plurality of biophysical properties, wherein the additional plurality of structural features includes at least one structural feature that is different from the plurality of structural features and the additional biophysical property is different from the biophysical property.

3. The method of claim 2, wherein the biophysical property is a temperature at which the Ig antibody unfolds and the plurality of structural features includes a number of polar regions of the Ig antibody and a number of hydrophobic regions of the Ig antibody.

4. The method of claim 1, further comprising:

determining a first set of Ig antibodies from among the plurality of Ig antibodies to train an additional second machine learning model to predict an additional biophysical property; and training, using a portion of the training data corresponding to the first set of Ig antibodies, the additional second machine learning model by determining one or more equations that include a plurality of variables and a plurality of weights.

5. The method of claim 4, further comprising:

testing the additional second machine learning model by:

determining a second set of Ig antibodies from among the plurality of Ig antibodies; and determining differences between first values of the additional biophysical property produced by the additional second machine learning model and second values of the additional biophysical property produced by the additional second machine learning model.

6. The method of claim 1, wherein the plurality of second machine learning models include:

a first machine learning model that uses first output from a first set of the plurality of first machine learning models to predict first values of a first biophysical property; and a second machine learning model that uses second output from a second set of the plurality of first machine learning models to predict second values of a second biophysical property.

7. The method of claim 6, wherein the first set of the plurality of first machine learning models include at least one machine learning model that predicts a structural feature that is different from an additional structural feature predicted by an additional machine learning model included in the second set of the plurality of second machine learning models.

8. The method of claim 1, wherein the plurality of second machine learning models include a Parafac model, a partial least squares model, or a non-parametric linkage scores model.

9. The method of claim 1, wherein:

the amino acid sequences of the plurality of Ig antibodies and the plurality of variants for the individual Ig antibodies are determined using at least one of mass spectrometry or Edman degradation;

the first structural features and the second structural features are determined using laser Ramen spectroscopy; and the first values of the plurality of biophysical properties and the second values of the plurality of biophysical properties are determined using at least one of size exclusion chromatography, UV-Vis spectrophotometry, differential scanning fluorimetry, a chemical unfolding assay, or self-interaction nanoparticle spectroscopy.

10. A computer-implemented method comprising:

generating individual encodings between individual proteins and a plurality of variants corresponding to the individual proteins based on (i) differences between amino acid sequences of the individual proteins and the plurality of variants corresponding to the individual proteins and (ii) one or more structural features corresponding to individual positions of the amino acid sequences of the individual proteins and the plurality of variants corresponding to the individual proteins;

obtaining training data that includes first data indicating values of biophysical properties of the individual proteins and the plurality of variants corresponding to the individual proteins and second data indicating structural features of the individual proteins and the plurality of variants corresponding to the individual proteins;

performing, based on the second data and the individual encodings, a first training process to generate a plurality of first machine learning models, wherein the plurality of first machine learning models include at least one of a random forests model, a convolutional neural network, or a k-Nearest Neighbor model coupled with a neural network and individual first machine learning models of the plurality of first machine learning models predict a presence or an absence of an individual structural feature;

performing, based on the first data, a second training process to generate a second machine learning model that is different from the plurality of first machine learning models and that predicts values for a biophysical property, wherein the second machine learning model includes a random forests model or a convolutional neural network;

obtaining an amino acid sequence of an additional protein;

determining, based on the amino acid sequence and utilizing the plurality of first machine learning models, positions of the additional protein that correspond to the one or more structural features of the structural features;

providing output from the plurality of first machine learning models as input to the second machine learning model, the output of each individual first machine learning model indicating a prediction of a number of positions of the additional protein that have the individual structural feature corresponding to the individual first machine learning model; and determining, based on the output from the plurality of first machine learning models, a value of the biophysical property of the additional protein.

11. The method of claim 10, further comprising:

obtaining an additional amino acid sequence of an additional variant of the additional protein; and determining, based on the amino acid sequence of the additional protein and the additional amino acid sequence of the additional variant and utilizing the plurality of first machine learning models, differences between one or more structural features of the additional protein and the additional variant.

12. The method of claim 10, further comprising:

generating a probability map indicating individual probabilities that a change in an amino acid located at an individual position of the amino acid sequence of the additional protein results in a change in a structural feature of the additional protein.

13. The method of claim 12, further comprising:

determining a number of variants of the additional protein based on the probability map.

14. A system comprising:

one or more processors; and one or more non-transitory computer-readable media to store computer-readable instructions that, when executed by the one or more processors, perform operations comprising:

generating individual encodings between individual proteins and a plurality of variants corresponding to the individual proteins based on (i) differences between amino acid sequences of the individual proteins and the plurality of variants corresponding to the individual proteins and (ii) one or more structural features corresponding to individual positions of the amino acid sequences of the individual proteins and the plurality of variants corresponding to the individual proteins;

obtaining training data including first data indicating values of biophysical properties of the individual proteins and the plurality of variants corresponding to the individual proteins and second data indicating structural features of the individual proteins and the plurality of variants corresponding to the individual proteins;

performing, based on the second data, a first training process to generate a plurality of first machine learning models corresponding to individual structural features of a plurality of structural features, wherein the plurality of first machine learning models include at least one of a random forests model, a convolutional neural network, or a k-Nearest Neighbor model coupled with a neural network and individual first machine learning models of the plurality of first machine learning models predict a presence or an absence of the individual structural features;

performing, based on the first data, a second training process to generate a second machine learning model corresponding to a biophysical property, the second machine learning model predicts values for the biophysical property and the second machine learning model includes a random forests model or a convolutional neural network;

obtaining an amino acid sequence of a protein, wherein the protein is not included in the number of individual proteins;

determining, based on the amino acid sequence and utilizing the plurality of first machine learning models, positions of the protein that correspond to one or more structural features of the structural features;

providing output from the plurality of first machine learning models as input to the second machine learning model, the output of each individual first machine learning model indicating a prediction of a number of positions of the protein that have an individual structural feature corresponding to the individual first machine learning model; and determining, based on the output from the plurality of first machine learning models and utilizing the second machine learning model, a value of the biophysical property for the protein.

15. The system of claim 14, wherein the one or more non-transitory computer-readable media store additional computer-readable instructions that, when executed by the one or more processors, perform additional operations comprising:

generating a probability map indicating individual probabilities that a change in an amino acid located at an individual position of the amino acid sequence of the additional protein results in a change in a structural feature of the additional protein.

16. The system of claim 15 wherein the one or more non-transitory computer-readable media store the additional computer-readable instructions that, when executed by the one or more processors, perform additional operations comprising:

determining a number of variants of the additional protein based on the probability map.

17. The system of claim 14, wherein the training data includes structural features of a plurality of proteins, structural features of variants of the individual proteins of the plurality of proteins, biophysical properties of the plurality of proteins, and biophysical properties of the variants of the individual proteins of the plurality of proteins.

18. The system of claim 17, wherein the one or more non-transitory computer-readable media store additional computer-readable instructions that, when executed by the one or more processors, perform additional operations comprising:

analyzing the training data to determine relationships between the structural features and the biophysical property.

\* \* \* \* \*